(12) United States Patent
Wauer et al.

(10) Patent No.: US 12,383,509 B2
(45) Date of Patent: Aug. 12, 2025

(54) TRANSDERMAL DELIVERY SYSTEM INCLUDING AN EMULSIFIER

(71) Applicant: LTS LOHMANN THERAPIE-SYSTEME AG, Andernach (DE)

(72) Inventors: Gabriel Wauer, Bad Neuenahr-Ahrweiler (DE); Frank Seibertz, Bad Breisig (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 16/641,741

(22) PCT Filed: Aug. 31, 2018

(86) PCT No.: PCT/EP2018/073498
§ 371 (c)(1),
(2) Date: Feb. 25, 2020

(87) PCT Pub. No.: WO2019/043172
PCT Pub. Date: Mar. 7, 2019

(65) Prior Publication Data
US 2020/0246276 A1     Aug. 6, 2020

(30) Foreign Application Priority Data
Sep. 4, 2017  (EP) .................................. 17189273

(51) Int. Cl.
*A61K 9/70*      (2006.01)
*A61K 31/196*    (2006.01)
(Continued)

(52) U.S. Cl.
CPC .......... *A61K 9/7053* (2013.01); *A61K 9/7069* (2013.01); *A61K 31/196* (2013.01);
(Continued)

(58) Field of Classification Search
None
See application file for complete search history.

(56) References Cited

U.S. PATENT DOCUMENTS 4,814,184 A * 3/1989 Aguadisch ........... A61K 9/7069
                                                      424/486
2004/0202707 A1* 10/2004 Muller .................... A61P 25/04
                                                      424/449

(Continued)

FOREIGN PATENT DOCUMENTS

EP         0281236 A2    9/1988
JP       S63-227517 A    9/1988

(Continued)

OTHER PUBLICATIONS

Becker et al. "Safety Assessment of Dimethicone Crosspolymers as Used in Cosmetics", International Journal of Toxicology, vol. 33 (Spplemental 2), 65-115 (Year: 2014).*

(Continued)

*Primary Examiner* — Isis A Ghali
(74) *Attorney, Agent, or Firm* — Sterne, Kessler, Goldstein & Fox P.L.L.C.

(57) ABSTRACT

The present invention relates to a transdermal therapeutic system (TTS) comprising an active agent-containing layer structure comprising A) a backing layer and B) a biphasic matrix layer, the biphasic matrix layer having a) a continuous, outer phase having a composition comprising 70 to 100% by weight of at least one polymer, b) a discontinuous, inner phase having a composition comprising the active agent and a dissolver for the active agent in amount sufficient so that the active agent forms a solution with the dissolver in the inner phase and c) an emulsifier in an amount of 0.1 to 20% by weight based on the biphasic (Continued)

matrix layer, processes of manufacture and uses thereof, corresponding methods of treatments therewith.

11 Claims, 9 Drawing Sheets

(51) Int. Cl.
```
A61K 31/485      (2006.01)
A61K 47/12       (2006.01)
A61K 47/34       (2017.01)
A61K 47/44       (2017.01)
A61P 29/00       (2006.01)
```

(52) U.S. Cl.
CPC ............ *A61K 31/485* (2013.01); *A61K 47/12* (2013.01); *A61K 47/34* (2013.01); *A61K 47/44* (2013.01); *A61P 29/00* (2018.01)

(56) References Cited

U.S. PATENT DOCUMENTS

| | | | | |
|---|---|---|---|---|
| 2004/0202710 A1* | 10/2004 | Muller | ................ | A61K 9/7069 |
| | | | | 424/449 |
| 2004/0234583 A1 | 11/2004 | Muller | | |
| 2009/0041694 A1* | 2/2009 | Pinzer | ................ | A61K 8/894 |
| | | | | 424/78.03 |
| 2010/0119585 A1* | 5/2010 | Hille | ................ | A61K 47/12 |
| | | | | 424/449 |
| 2015/0148355 A1* | 5/2015 | Trimble | ................ | A61K 9/06 |
| | | | | 514/263.36 |
| 2016/0008294 A1* | 1/2016 | Hille | ................ | A61K 31/485 |
| | | | | 424/443 |
| 2016/0101050 A1* | 4/2016 | Lee | ................ | A61K 47/26 |
| | | | | 424/400 |

FOREIGN PATENT DOCUMENTS

| | | | |
|---|---|---|---|
| JP | 2007-505107 A | | 3/2007 |
| JP | 2007-532577 A | | 11/2007 |
| JP | 2016-520638 A | | 7/2016 |
| RU | 2539397 C2 | * | 1/2015 |
| WO | WO 2005/025548 A1 | | 3/2005 |
| WO | WO 2005/099676 A2 | | 10/2005 |
| WO | WO 2011/076879 A1 | | 6/2011 |
| WO | WO 2014/079573 A1 | | 5/2014 |
| WO | WO 2014/195352 A1 | | 12/2014 |

OTHER PUBLICATIONS

Lee et al. "A study for polyol-in-oil type lip makeup cosmetics with natural pigments", J. Soc. Cosmet. Scientists Korea, vol. 39, No. 1, March, 65-73 (Year: 2013).*

International Search Report for International Application No. PCT/EP2018/073498, European Patent Office, Netherlands, mailed Oct. 11, 2018, 4 pages.

Dow Corning® 9011 Silicone Elastomer Blend, "Cyclopentasiloxane and PEG-12 Dimethicone Crosspolymer," Dow Corning, Apr. 5, 2016, 3 pages.

* cited by examiner

13A

13B

13C

13D

13E

13F

13G

13H

13I

13J

13K

13L

13M

13N

13O

13P

13Q

13R

TRANSDERMAL DELIVERY SYSTEM INCLUDING AN EMULSIFIER

TECHNICAL FIELD OF THE INVENTION

The present invention relates to a transdermal therapeutic system (TTS) comprising a biphasic structure including a discontinuous, inner phase dispersed in a continuous, outer phase, processes of manufacture and uses thereof, corresponding methods of treatments therewith.

BACKGROUND OF THE INVENTION

Transdermal therapeutic systems (TTS) can mainly be distinguished in two types of TTS for active agent delivery, the so-called matrix-type TTS and the so-called reservoir-type TTS.

In a matrix-type TTS, the active agent is homogeneously dissolved and/or dispersed within a polymeric carrier, i.e. the matrix, which forms with the active agent and optionally remaining ingredients a matrix layer. In such a system, the matrix layer controls the release of the active agent from the TTS.

In a reservoir-type TTS, the active agent is present in a liquid reservoir. In such a system, the release of the active agent is preferably controlled by a rate-controlling membrane. In particular, the reservoir is sealed between the backing layer and the rate-controlling membrane. Furthermore, the reservoir-type TTS typically additionally comprises a skin contact layer, wherein the reservoir layer and the skin contact layer may be separated by the rate-controlling membrane. An advantage of the reservoir-type TTS is the high active agent utilization due to the often oversaturated reservoir. However, in the event of damage of the reservoir, dose dumping may occur.

A microreservoir TTS is considered in the art to be a mixed form of the matrix-type TTS and the reservoir-type TTS and differs from a homogeneous single phase matrix-type TTS and a reservoir-type TTS in the concept of active agent transport and active agent delivery. A microreservoir TTS comprises at least two phases, namely a dispersed inner phase and an outer phase surrounding the inner phase deposits. A limited solubility of the inner phase in the outer phase is a prerequisite to provide such a biphasic structure. Microreservoir TTS are usually characterized by an improved active agent utilization compared to matrix-type TTS, as the active agent contained in the inner phase only slightly dissolves in the outer phase, thus supporting the ambition to shift from the microreservoir system towards the skin. A current problem of the microreservoir TTS is the insufficient stabilization of the biphasic structure, in particular during the process of manufacture of the TTS.

For example, a biphasic composition to be coated is usually prepared batch wise, and is then stored for some time until the coater is ready to coat the composition. The time between the preparation of the composition and the coating of the composition in a normal production routine can be almost zero, if after mixing the composition will be transferred to the coating station and is coated directly and may be as long as several days, e.g. four to six days, to store the composition during the time of a failure of the coater or a weekend or other reasons for a coating process interruption. After the biphasic composition is prepared in the mixing step the system tends towards a phase separation. The inner phase deposits tend to coalesce and the formed larger deposits may sediment during storage.

Additionally, during the coating process, shear forces act upon the biphasic coating composition resulting in a strong coalescence of the inner phase and an uncontrolled distribution of the fused inner phase deposits within the coating composition and in the final biphasic matrix layer.

Without wishing to be bound to any theory it is believed that the size and size distribution of the deposits influences the active agent delivery from the TTS. Large deposits release the active agent too fast and provide for an undesired high active agent delivery at the beginning of the dosing period (also known as "drug burst") and a failure of the system for longer dosing periods since the loss of active agent at the beginning will lead to a loss of driving force later in the dosing period. The permeation of the active agent is thus not predictable and may be too fast, not long enough, and not sufficiently continuous.

There is thus a need to sufficiently control the size and size distribution of the deposits. The deposits must in particular be hindered in fusing during the storing time between mixing and coating and during the coating process.

To reduce the starting size of the deposits (droplets) in the biphasic coating composition the composition may be homogenized. However, coalescence of the inner phase can still be observed during storage of the biphasic coating composition and, in particular, under shear stress during the coating process.

WO 2014/195352 relates to a microreservoir TTS for the transdermal administration of buprenorphine and shows that fusing of the deposits and the corresponding size increase of the deposits can be controlled by the use of a viscosity-increasing substance. It is stated that the viscosity-increasing substance increases the viscosity of the deposits (inner phase) within the adhesive solution (outer phase) during the production and within the adhesive matrix (outer phase) during the storage of the dried buprenorphine-containing layer.

It is stated in WO 2014/195352 that a roller coater is necessary to provide the necessary scale up and the necessary coating precision for commercial scale production. The shearing force applied to the coating mixture during coating in a roller coater is different and higher than on a laboratory scale coating technique like such as when using the Erichsen coater. The shear force in a roller coater causes additional fusion of the deposits. Although it was shown that the viscosity-increasing substance has a stabilizing effect on the biphasic system, the deposits of the matrix layer are still subject to a certain size increase under high shear forces, like the shear forces that are applied during the preparation of the biphasic matrix layer using a roller coater. Thus, it is still desirable to hinder the deposits in fusing, in particular, during the process of manufacturing of a biphasic system, particularly during the coating process.

As the tolerance for a variability in active agent delivery is very limited in view of a possible over- or underdosing and a possible skin irritation, for example, caused by an excessive release of active agent at the beginning of the application period, the variability of microreservoir TTS needs to be sufficiently controlled.

There is thus a need in the art for an improved microreservoir TTS.

All references and publications cited herein are hereby incorporated by reference in their entirety for all purposes.

OBJECTS AND SUMMARY OF THE INVENTION

It is an object of certain embodiments of the present invention to provide a microreservoir TTS for the transdermal administration of an active agent with an improved stability of the biphasic matrix layer.

It is an object of certain embodiments of the present invention to provide a microreservoir TTS for the transdermal administration of an active agent with an improved resistance to shear forces.

It is an object of certain embodiments of the present invention to provide a microreservoir TTS for the transdermal administration of an active agent with an improved active agent release.

It is an object of certain embodiments of the present invention to provide a microreservoir TTS for the transdermal administration of an active agent with a more constant and continuous active agent delivery.

It is a further object of the present invention to provide a microreservoir TTS for the transdermal administration of an active agent with a high active agent utilization, i.e. a TTS, which does not require a high excess amount of the active agent in order to provide suitable active agent delivery properties during an administration period to the skin of a patient for at least 1 day (24 hours), for at least 3 days (72 hours), or about 7 days (168 hours).

It is an object of certain embodiments of the present invention to provide an improved process of manufacturing a microreservoir TTS.

It is an object of certain embodiments of the present invention to provide an improved reproducibility in the process a manufacturing of a microreservoir TTS.

It is an object of certain embodiments of the present invention to improve the storage properties of a biphasic composition.

It is an object of certain embodiments of the present invention to control the size of the inner phase deposits of a biphasic composition.

It is an object of certain embodiments of the present invention to prevent a size increase of the inner phase deposits of a biphasic composition during the process of manufacturing a TTS.

It is an object of certain embodiments of the present invention to provide an improved resistance of the inner phase of a biphasic composition towards coalescence.

These objects and others are accomplished by the present invention which according to one aspect relates to a transdermal therapeutic system for the transdermal administration of an active agent comprises an active agent-containing layer structure, the active agent-containing layer structure comprising A) a backing layer, and B) a biphasic matrix layer, the biphasic matrix layer having a) a continuous, outer phase having a composition comprising 70 to 100% by weight of at least one polymer, b) a discontinuous, inner phase having a composition comprising the active agent and a dissolver (e.g. carboxylic acid) for the active agent in amount sufficient so that the active agent forms a solution with the dissolver in the inner phase, wherein the discontinuous, inner phase forms dispersed deposits in the continuous, outer phase, and c) an emulsifier in an amount of 0.1 to 20% by weight based on the biphasic matrix layer, wherein the emulsifier is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

According to one specific aspect, the invention relates to a use of an emulsifier based on polysiloxane in a transdermal therapeutic system with an active agent-containing biphasic matrix layer having a discontinuous, inner phase and a continuous, outer phase for controlling the maximum sphere size of the discontinuous, inner phase of the biphasic matrix layer.

According to one specific aspect, the invention relates to a use of an emulsifier selected from the group consisting of an emulsifier based on polyisobutylene, an emulsifier based on ethoxylated castor oil, and an emulsifier based on poloxamer in a transdermal therapeutic system with an active agent-containing biphasic matrix layer having a discontinuous, inner phase and a continuous, outer phase for controlling the maximum sphere size of the discontinuous, inner phase of the biphasic matrix layer.

According to one specific aspect, the invention relates to a method of stabilizing a biphasic coating mixture that comprises a discontinuous, inner phase having a composition comprising an active agent and a dissolver (e.g. carboxylic acid) for the active agent in amount sufficient so that the active agent forms a solution with the dissolver in the inner phase, the inner phase forming dispersed deposits in a continuous, outer phase comprising a polymer, by mixing the biphasic coating mixture with an emulsifier that is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

According to one specific aspect, the invention relates to a method of manufacture of a biphasic matrix layer comprising the steps of: (1) preparing a stabilized biphasic coating mixture in accordance with the previous paragraph, (2) coating the stabilized biphasic coating mixture on a film in an amount to provide a desired area weight, (3) evaporating the solvents to provide a biphasic matrix layer with the desired area weight.

According to one specific aspect, the invention relates to method of manufacture of a transdermal therapeutic system in accordance with the present invention, comprising the steps of: (1) providing a stabilized biphasic coating mixture comprising (a) a polymer, (b) an active agent, (c) a dissolver for the active agent, (d) an emulsifier, (e) a solvent, (f) optionally a viscosity-increasing substance, (2) coating the stabilized biphasic coating mixture on a film in an amount to provide a desired area weight, (3) evaporating the solvents to provide a biphasic matrix layer with the desired area weight, (4) laminating the biphasic matrix layer to a backing layer to provide an active agent-containing layer structure, (5) optionally laminating the active agent-containing layer structure to an additional skin contact layer, (6) optionally punching the individual systems from the buprenorphine-containing self-adhesive layer structure with the desired area of release, and (7) optionally adhering to the individual systems an active-free self-adhesive layer structure comprising also a backing layer and an active agent-free pressure-sensitive adhesive layer and which is larger than the individual systems of buprenorphine-containing self-adhesive layer structure.

Definitions

Within the meaning of this invention, the term "transdermal therapeutic system" (TTS) refers to a system by which the active agent (e.g. buprenorphine or diclofenac) is administered via transdermal delivery, for example, to the local area to be treated or the systemic circulation and refers to the entire individual dosing unit that is applied, after removing an optionally present release liner, to the skin of a patient, and which comprises a therapeutically effective amount of active agent in an active agent-containing layer structure and optionally an additional adhesive overlay on top of the active agent-containing layer structure. The active agent-containing layer structure may be located on a release liner (a detachable protective layer), thus, the TTS may further comprise a release liner. Within the meaning of this invention, the term "TTS" in particular refers to systems providing transdermal delivery, excluding active delivery for example via iontophoresis or microporation. Transdermal therapeutic systems may also be referred to as transdermal drug delivery systems (TDDS) or transdermal delivery systems (TDS).

The TTS having a biphasic matrix layer according to this invention are also known as "microreservoir TTS".

Within the meaning of this invention, the term "active agent-containing layer structure" refers to the layer structure containing a therapeutically effective amount of the active agent and comprises a backing layer and at least one biphasic matrix layer. Preferably, the active agent-containing layer structure is an active agent-containing self-adhesive layer structure.

The term "therapeutically effective amount" refers to a quantity of active agent in the TTS sufficient to provide a treatment, if administered by the TTS to a patient, such as exemplarily the treatment of pain. A TTS usually contains more active in the system than is in fact provided to the skin and the local area to be treated or the systemic circulation. This excess amount of active agent is usually necessary to provide enough driving force for the delivery from the TTS to the local area to be treated or the systemic circulation.

Within the meaning of this invention, the terms "active", "active agent", and the like (such as exemplarily the term "buprenorphine" or "diclofenac"), refer to the active agent (such as exemplarily buprenorphine or diclofenac) in any pharmaceutically acceptable chemical and morphological form and physical state. These forms include without limitation the active agent in its free base/free acid form, protonated or partially protonated foi III of the active agent, their salts, cocrystals and in particular acid/base addition salts formed by addition of an inorganic or organic acid/base such as exemplarily buprenorphine hydrochloride or buprenorphine maleate, solvates, hydrates, clathrates, complexes and so on, as well as active agents in the form of particles which may be micronized, crystalline and/or amorphous, and any mixtures of the aforementioned forms. In the present invention, the active agent forms a solution with the dissolver in the inner phase of a biphasic matrix layer. The active agent may nevertheless be in part dispersed in the outer phase of the biphasic matrix layer.

When the active agent is mentioned to be used in a particular form in the manufacture of the TTS, this does not exclude interactions between this form of the active and other ingredients of the active agent-containing layer structure, e.g. salt formation or complexation, in the final TTS. This means that, even if the active agent is included in its free base/acid form, it may be present in the final TTS in protonated or partially protonated/or deprotonated or partially deprotonated form or in the form of an acid addition salt, or, if it is included in the form of a salt, parts of it may be present as free base in the final TTS.

The active agent starting material included in the TTS during manufacture of the TTS may be in the form of particles and/or dissolved. The active agent may e.g. be present in the active agent-containing layer structure in the form of particles and/or dissolved.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "deposit" as used in reference to "dispersed deposits" refers to distinguishable, e.g., visually distinguishable, areas within the biphasic matrix layer. Such deposits are e.g., droplets and spheres. Within the meaning of this invention, the term droplets is preferably used for the deposits in the biphasic coating composition and the terms spheres is preferably used for the deposits in the biphasic matrix layer. The deposits may be identified by use of a microscope. The sizes of the deposits can be determined by an optical microscopic measurement (for example by Leica MZ16 including a camera, for example Leica DSC320) by taking pictures of the biphasic matrix layer at different positions at an enhancement factor between 10 and 400 times, depending on the required limit of detection. By using imaging analysis software, the sizes of the deposits can be determined.

Within the meaning of this invention, the size of the deposits refers to the diameter of the deposits as measured using a microscopic picture of the biphasic matrix layer.

Within the meaning of this invention, the term "matrix layer" refers to a layer containing the active agent and providing the area of release. The matrix layer of the TTS according to this invention is biphasic, i.e. a biphasic matrix layer, having a continuous, outer phase comprising 70 to 100% by weight of at least one polymer and a discontinuous, inner phase having a composition comprising the active agent and a dissolver for the active agent in amount sufficient so that the active agent forms a solution with the dissolver in the inner phase. If at least one polymer in the continuous, outer phase is a pressure-sensitive adhesive polymer, the biphasic matrix layer may also represent the adhesive layer of the TTS, so that no additional skin contact layer is present. Alternatively, an additional skin contact layer may be present as adhesive layer, and/or an adhesive overlay is provided. The additional skin contact layer is typically manufactured such that it is active agent-free. However, due to the concentration gradient, the active agent will migrate from the biphasic matrix layer to the additional skin contact layer over time, until an equilibrium is reached. The additional skin contact layer may be present on the biphasic matrix layer or separated from the biphasic matrix layer by a membrane, preferably a rate controlling membrane. Preferably, the biphasic matrix layer has sufficient adhesive properties, i.e. is self-adhesive, so that no additional skin contact layer is present.

Preferably, the biphasic matrix layer according to the invention is obtained after coating and drying the solvent-containing coating composition as described herein (solvent-based matrix layer). Such a solvent-based matrix layer can also be described as dried biphasic matrix layer. Alternatively, a biphasic matrix layer is obtained after melt-coating and cooling (hot-melt-based matrix layer). The biphasic matrix layer according to the invention is preferably a dried biphasic layer. The (active agent-containing) biphasic matrix layer may also be manufactured by laminating two or more such solidified layers (e.g. dried or cooled layers) of the same composition to provide the desired area weight.

Within the meaning of this invention, the term "pressure-sensitive adhesive" (also abbreviated as "PSA") refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive biphasic matrix layer or in the form of an additional layer, i.e. a pressure sensitive adhesive skin contact layer. An adhesive overlay may still be employed to advance adhesion. The pressure-sensitive adhesive properties of a pressure-sensitive adhesive depend on the polymer or polymer composition used.

Within the meaning of this invention, the term "skin contact layer" refers to the layer included in the active agent-containing layer structure to be in direct contact with the skin of the patient during administration. This may be the biphasic matrix layer. When the TTS comprises an additional skin contact layer, the other layers of the active agent-containing layer structure do not contact the skin and do not necessarily have self-adhesive properties. As outlined above, an additional skin contact layer attached to the biphasic matrix layer may over time absorb parts of the active agent. An additional skin contact layer may be used to enhance adherence. The sizes of an additional skin contact layer and the biphasic matrix layer are usually coextensive and correspond to the area of release. However, the area of the additional skin contact layer may also be greater than the area of the biphasic matrix layer. In such a case, the area of release still refers to the area of the biphasic matrix layer.

Within the meaning of this invention, the term "area weight" refers to the weight of a specific layer, e.g. of the biphasic matrix layer, after coating and drying or after melt-coating and cooling, provided in $g/m^2$. The area weight values are subject to a tolerance of ±10%, preferably ±7.5%, due to manufacturing variability.

If not indicated otherwise "%" refers to weight-%.

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2000, preferably above 5000 and more preferably above 10,000 Dalton. Correspondingly, compounds with a molecular weight below 2000, preferably below 5000 or more preferably below 10,000 Dalton are usually referred to as oligomers.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer that may provide occlusive or non-occlusive properties and an adhesive layer. Preferably, the backing layer of the adhesive overlay provides non-occlusive properties.

Within the meaning of this invention, the term "backing layer" refers to a layer which supports the biphasic matrix layer or forms the backing of the adhesive overlay. At least one backing layer in the TTS and usually the backing layer of the biphasic matrix layer is substantially impermeable to the active agent contained in the layer during the period of storage and administration and thus prevents active loss or cross-contamination in accordance with regulatory requirements. Preferably, the backing layer is also occlusive, meaning substantially impermeable to water and water-vapor. Suitable materials for a backing layer include polyethylene terephthalate (PET), polyethylene (PE), ethylene vinyl acetate-copolymer (EVA), polyurethanes, and mixtures thereof. Suitable backing layers are thus for example PET laminates, EVA-PET laminates and PE-PET laminates. Also suitable are woven or non-woven backing materials.

The TTS according to the present invention can be characterized by certain parameters as measured in an in vitro skin permeation test.

In general, the in vitro permeation test is performed in a Franz diffusion cell, with human or animal skin and preferably with dermatomed split-thickness human skin with a thickness of from 200 μm to 800 μm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylenglycol, PEG 400 so that a receptor medium may e.g. contain 60 vol-% phosphate buffer pH 5.5, 30 vol-% dipropylenglycol and 10 vol-% acetonitrile.

Where not otherwise indicated, the in vitro permeation test is performed with dermatomed split-thickness human skin with a thickness of 800 μm and an intact epidermis, and with phosphate buffer pH 5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in $\mu g/cm^2$ and relates to the amount of active permeated in a sample interval at certain elapsed time. E.g., in an in vitro permeation test as described above, wherein the amount of active permeated into the receptor medium has been e.g. measured at hours 0, 2, 4, 8, 12 and 24, the "permeated amount" of active can be given e.g. for the sample interval from hour 8 to hour 12 and corresponds to the measurement at hour 12, wherein the receptor medium has been exchanged completely at hour 8.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in µg/cm²-hr and is calculated from the permeated amount in said sample interval as measured by in vitro permeation test as described above in µg/cm², divided by the hours of said sample interval. E.g. the skin permeation rate in an in vitro permeation test as described above, wherein the amount of active permeated into the receptor medium has been e.g. measured at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters "permeated amount" and "skin permeation rate" (as well as "cumulative permeated amount" and "cumulative skin permeation rate") refer to mean values calculated from at least 3 in vitro permeation test experiments. Where not otherwise indicated, the standard deviation (SD) of these mean values refer to a corrected sample standard deviation, calculated using the formula:

$$SD = \sqrt{\frac{1}{n-1} \sum_{i=1}^{n} (x_i - \overline{x})^2}$$

wherein n is the sample size, $\{x_1, x_2, \ldots x_n\}$ are the observed values and $\overline{x}$ is the mean value of the observed values.

To allow a comparison of absolute mean values between studies, a reference formulation including the same active ingredient may be used as internal standard. For example, for a diclofenac delivery system the commercial reference product Voltaren® Patch and for a buprenorphine delivery system the commercial reference product Norspan®, or in the future any commercial product based on these systems, may be used as internal standard. A comparison of the values, e.g. the mean cumulative of the respective reference products in the earlier and later study can be used to obtain a correction factor to take into account differences from study to study.

Within the meaning of this invention, the term "extended period of time" relates to a period of at least or about 24 h, at least or about 48 h, at least or about 84 h, at least or about 168 h, at least or about 1 day, at least or about 3.5 days, or at least or about 7 days, or to a period of about 24 h to about 168 h or 1 to 7 day(s), or about 24 h to about 84 h or 1 to 3.5 day(s).

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention, the terms "coating composition" and "coating mixture" refer to a composition comprising all components of the matrix layer in a solvent, which may be coated onto the backing layer or release liner to form the matrix layer upon drying.

Within the meaning of this invention, the term "pressure sensitive adhesive composition" refers to a pressure sensitive adhesive at least in mixture with a solvent (e.g. n-heptane or ethyl acetate).

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, toluene and mixtures thereof. The term "dissolver for the active agent" is to be distinguished therefrom in that it refers only to a solvent which can solubilize the active agent and with which it is possible to disperse the active agent-dissolver mixture in the form of small deposits (e.g. droplets) in a matrix layer prepared on the basis of polymers.

BRIEF DESCRIPTION OF THE D WINGS

DETAILED DESCRIPTION

TTS Structure

Figure 1A:
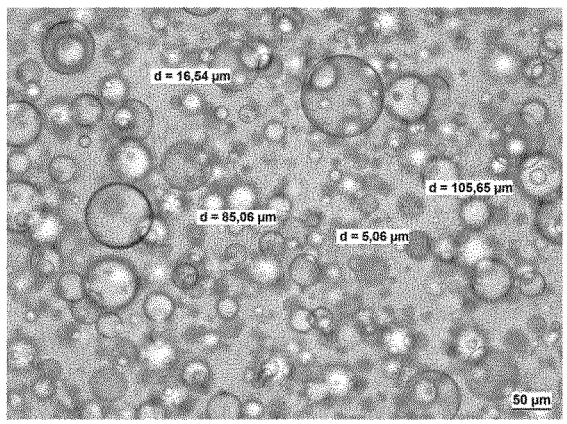
FIG. 1A depicts the diclofenac-containing biphasic coating mixture of Comparative Example 1.

According to a certain embodiment of the invention the transdermal therapeutic system for the transdermal administration of an active agent comprises an active agent-containing layer structure, the active agent-containing layer structure comprising
A) a backing layer, and
B) a biphasic matrix layer, the biphasic matrix layer having
a) a continuous, outer phase having a composition comprising 70 to 100% by weight of at least one polymer,
b) a discontinuous, inner phase having a composition comprising the active agent and a dissolver for the active agent in amount sufficient so that the active agent forms a solution with the dissolver in the inner phase, wherein the discontinuous, inner phase forms dispersed deposits in the continuous, outer phase, and
c) an emulsifier in an amount of 0.1 to 20% by weight based on the biphasic matrix layer.

Suitable emulsifiers are selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

Without wishing to be bound to any theory it is believed that the emulsifier stabilizes the biphasic structure (the inner phase dispersed in the outer phase) during the production and during the storage of the TTS, in particular, during the process of manufacture of the biphasic matrix layer when shear forces are applied. Due to a more homogeneous size distribution of the inner phase deposits the resistance towards coalescence increases and the diameter of the deposits does not increase significantly.

According to a certain embodiment of the present invention, the biphasic matrix layer is the skin contact layer of the TTS.

According to a certain other embodiment of the present invention, an additional rate-controlling membrane and/or an additional skin contact layer (active agent free or containing) may be present.

According to certain embodiments of the invention, the TTS comprises in addition to the active agent-containing self-adhesive layer structure attached thereto a larger active agent-free self-adhesive layer structure, e.g., a peripheral adhesive or an adhesive overlay, for enhancing the adhesive properties of the overall transdermal therapeutic system. Said active agent-free self-adhesive layer structure comprises also a backing layer. In certain embodiments, this additional layer is beige colored. The area of said second active agent-free self-adhesive layer structure adds to the overall size of the TTS but does not add to the area of release. The pressure-sensitive adhesive in the active agent-containing and the active agent-free self-adhesive layer structures may be the same or different.

In accordance with the invention, the active agent-containing layer structure comprises a backing layer and an active agent-containing biphasic matrix layer. In a certain embodiment, the active agent-containing layer structure consists of these two elements.

In a preferred embodiment of the present invention, the active agent-containing layer structure is an active agent-containing self-adhesive layer structure, comprising a backing layer and a (active agent-containing) pressure-sensitive adhesive biphasic matrix layer. The active agent-containing layer structure may further comprise an additional skin contact layer.

Biphasic Matrix Layer

The biphasic matrix layer of the TTS according to this invention contains dispersed deposits of an inner phase in a continuous, outer phase, and an emulsifier.

In accordance with the invention, the continuous, outer phase of the active agent-containing biphasic layer is a composition comprising 70% to 100% by weight of at least one polymer.

In accordance with the invention, the discontinuous, inner phase is a composition comprising the active agent and a dissolver for the active agent in amount sufficient so that the active agent forms a solution with the dissolver in the inner phase.

In accordance with the invention, the emulsifier is contained in the biphasic matrix layer in an amount of 0.1 to 20% by weight and is selected from a group consisting of emulsifiers which, when blended at about 500 to 1500 rpm with an equal weight amount of the composition of the continuous, outer phase of the biphasic system for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

In a preferred embodiment of the present invention, the emulsifier is contained in an amount of 0.1 to less than 20%, or 0.5 to 10%, or 0.5 to 8%, or 0.5 to 5% by weight based on the biphasic matrix layer.

The active agent may be contained in an amount of from 1 to 30%, preferably in an amount of from 1 to 15%, more preferably in an amount of from 2 to 12% by weight based on the biphasic matrix layer.

The active agent may also be contained in an amount of from 0.1 to 5 mg/cm$^2$, preferably in an amount of from 0.5 to 1.5 mg/cm$^2$, more preferably in an amount of from 3 to 5 mg/cm$^2$ based on the biphasic matrix layer.

The dissolver for the active agent is present in an amount sufficient so that the active agent forms a solution with the dissolver in the inner phase. The amount of dissolver for the active agent contained in the biphasic matrix layer thus depends on the active agent and the dissolver.

In a preferred embodiment of the present invention, the dissolver for the active agent is contained in an amount of from 2 to 20%, preferably in an amount of from 5 to 15%, more preferably in an amount of from 6 to 12% by weight based on the biphasic matrix layer.

In a preferred embodiment of the present invention, the dissolver for the active agent is selected from the group consisting of carboxylic acids (e.g. $C_3$ to $C_{24}$), long-chain alcohols with more than four carbon atoms (e.g. $C_5$ to $C_{26}$), polyoxyethylene ethers of fatty alcohols, long-chain esters with more than four carbon atoms (e.g. $C_5$ to $C_{26}$), or mixtures thereof.

In a preferred embodiment of the present invention, the dissolver for the active agent is selected from the group consisting of carboxylic acids (e.g. $C_3$ to $C_{24}$), long-chain alcohols with more than four carbon atoms (e.g. $C_5$ to $C_{26}$), fatty alcohols, polyoxyethylene ethers of fatty alcohols, long-chain esters with more than four carbon atoms (e.g. $C_5$ to $C_{26}$), fatty acid esters or mixtures thereof. Preferably, the active agent is in solution in a carboxylic acid to form an active agent-carboxylic acid mixture in the discontinuous, inner phase of the biphasic matrix layer.

In a preferred embodiment of the present invention, the dissolver for the active agent is selected from the group consisting of carboxylic acids, fatty alcohols, polyoxyethylene ethers of fatty alcohols, fatty acid esters, or mixtures thereof. Preferably, the active agent is in solution in a carboxylic acid to form an active agent-carboxylic acid mixture in the discontinuous, inner phase of the biphasic matrix layer.

Suitable carboxylic acids may be selected from the group consisting of $C_3$ to $C_{24}$ carboxylic acids including oleic acid, linoleic acid, linolenic acid, levulinic acid, and mixtures thereof.

According to a certain embodiment of the present invention, where buprenorphine is used as an active agent, the biphasic matrix layer contains dispersed deposits of buprenorphine dissolved in levulinic acid.

According to a certain other embodiment of the present invention, where diclofenac is used as an active agent, the biphasic matrix layer contains dispersed deposits of diclofenac dissolved in oleic acid.

Levulinic acid and oleic acid are sparingly soluble in the organic solvents of the polymer adhesives. Consequently, the liquid mixture of active agent and such dissolvers for the active agent (levulinic acid or oleic acid) can be dispersed in the polymer mixture, with the dispersion being retained following removal of the organic solvent. In a matrix layer of this kind, the solubility of the active agent is dependent virtually only on the amount of the dissolver for the active agent.

In a certain preferred embodiment of the present invention, the carboxylic acid (e. g. oleic acid or levulinic acid) is contained in an amount of from 2 to 20%, preferably from 5 to 15%, in particular from 6 to 12%, by weight based on the biphasic matrix layer.

In yet another embodiment of the present invention, the carboxylic acid (e. g. oleic acid or levulinic acid) and the active agent are contained in the transdermal therapeutic system in an amount ratio of from 0.3:1 to 5:1, preferably from 0.5:1 to 2:1, in particular from 2:1 to 5:1.

Since the carboxylic acid, such as e.g., the levulinic acid, can likewise be absorbed through the skin, the amount in the TTS may become less as the time of application elapses, and may lead to a reduction of the solubility of the active agent, such as e.g. buprenorphine. As a result, the decrease in the thermodynamic activity of the active agent, such as e.g. buprenorphine, due to depletion is then compensated by the reduced drug solubility in the active agent/carboxylic acid deposits, e.g. buprenorphine/levulinic acid deposits or the diclofenac/oleic acid deposits.

The biphasic matrix layer according to this invention may have an area weight of more than 60 g/m$^2$, or of more than 60 g/m$^2$ to 200 g/m$^2$, preferably of more than 70 m/g$^2$ to 120 g/m$^2$, more preferably of from 80 to 120 g/m$^2$, and even more preferred of from 80 to 100 g/m$^2$.

According to a certain embodiment, the biphasic matrix layer has an area weight of from 80 to 120 g/m$^2$ and diclofenac sodium is contained in an amount of from 1 to 15% by weight of the biphasic layer.

According to a certain embodiment, the biphasic matrix layer has an area weight of from 80 to 120 g/m$^2$ and buprenorphine base is contained in an amount of from 1 to 15% by weight of the biphasic layer.

In a preferred embodiment of the present invention, the biphasic matrix layer is a pressure-sensitive adhesive biphasic matrix layer.

According to a certain embodiment, the biphasic matrix layer is obtained from a solvent-containing biphasic coating mixture after coating on a film and evaporating the solvents.

In a certain embodiment of the present invention, the content of the discontinuous, inner phase in the biphasic matrix layer is from 5 to 40% by volume based on the volume of the biphasic matrix layer.

In accordance with the present invention, the dispersed deposits may have a maximum sphere size of less than 50 preferably less than 40 more preferably less than 30 μm in particular less than 20 μm. The size of the inner phase deposits (spheres) can be determined by an optical microscopic measurement as described in more detail above.

In a certain embodiment of the present invention, the biphasic matrix layer further comprises a viscosity-increasing substance, which is preferably contained in an amount of from about 0.1% to about 15%, preferably from about 0.1% to about 8% by weight of the biphasic matrix layer.

Suitable viscosity-increasing substances may be selected from the group consisting of cellulose derivatives such as methylcellulose, ethylcellulose, hydroxyethylcellulose, hydroxypropylcellulose, hydroxypropylmethylcellulose, carboxymethylcellulose, sodium carboxymethylcellulose, microcrystalline cellulose, high molecular mass polyacrylic acids and/or their salts and/or their derivatives such as esters, polyvinylpyrrolidone, colloidal silicone dioxide, sodium alginate, tragacanth, xanthan gum, bentonite, carageenan and guar gum, and mixtures thereof. In a certain embodiment, the TTS according to the invention does not contain such a viscosity-increasing substance.

In certain embodiments of the present invention where a viscosity-increasing substance is contained, the viscosity-increasing substance is polyvinylpyrrolidone, more preferably soluble polyvinylpyrrolidone. The term "soluble polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F. In particular, the viscosity-increasing substance is a soluble polyvinylpyrrolidone having a K-Value of 30 or 90, preferably of 90. Within the meaning of this invention, the K-Value refers to a value calculated from the relative viscosity of polyvinylpyrrolidone in water according to the Ph.Eur. and USP monographs for "Povidone".

The biphasic matrix layer of the TTS according to the invention may further comprise one or more anti-oxidants. Suitable anti-oxidants are sodium metabisulfite, ascorbyl palmitate, tocopherol and esters thereof, ascorbic acid, butylhydroxytoluene, butylhydroxyanisole or propyl gallate, preferably sodium metabisulfite, ascorbyl palmitate and tocopherol. The anti-oxidants may be conveniently present in an amount of from about 0.001 to about 0.5% of the biphasic matrix layer.

The biphasic matrix layer according to the invention may further comprise in addition to the above mentioned ingredients other various excipients or additives, for example from the group of solubilizers, fillers, tackifiers, substances which influence the barrier properties of the stratum corneum in the sense of increasing the active agent permeability, pH regulators, and preservatives.

In general, it is preferred according to the invention that no further additives are required. In certain embodiments, no additives are present in the TTS.

When using an additional skin contact layer, the ingredients of the biphasic matrix layer such as the dissolver for the active agent, the active agent, the optional viscosity-increasing substance and optional additional excipients or additives may over time migrate into the additional skin contact layer. This however depends on the ingredients and the material of the skin contact layer.

In certain embodiments of the present invention, the biphasic matrix layer comprises the active agent in solution in a carboxylic acid (e. g. oleic acid or levulinic acid) and a viscosity-increasing substance (e. g. polyvinylpyrrolidone) to form a viscosity-increasing substance-, carboxylic acid-, and active agent-containing mixture in the discontinuous, inner phase of the biphasic layer.

In certain other embodiments of the present invention, the biphasic matrix layer comprises the active agent in solution in a carboxylic acid (e. g. oleic acid or levulinic acid) and no viscosity-increasing substance (e. g. polyvinylpyrrolidone) is present in the biphasic matrix layer.

Emulsifier

In accordance with the invention, the transdermal therapeutic system comprises an emulsifier in an amount of 0.1 to 20% by weight based on the biphasic matrix layer, wherein the emulsifier is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube. If the phase separation is observed to be 20% of more, it is to be understood within the present invention that the tested emulsifier is not suitable.

The blending for the emulsifier test may be conducted with a mechanical shaker, for example with a IKA Vibrax-VXR, wherein the blending is adjusted between steps 3 to 5. However, also other mechanical shakers may be used.

The biphasic matrix layer may contain 0.1 to less than 20%, preferably 0.5 to 10%, more preferably 0.5 to 8%, and in particular 0.5 to 5%, by weight of the emulsifier according to the present invention.

Suitable emulsifiers according to the present invention are selected from the group consisting of an emulsifier based on polysiloxane, an emulsifier based on polyisobutylene, an emulsifier based on ethoxylated castor oil, an emulsifier based on poloxamer, and mixtures thereof.

In a certain embodiment of the present invention, the emulsifier is based on polysiloxane. Preferably, the emulsifier according to the present invention comprises at least one polydimethylsiloxane copolymerized or crosspolymerized with polyethylene glycol, wherein preferably the at least one polydimethylsiloxane is copolymerized with polyethylene glycol and polypropylene glycol. The polyethylene glycol used for copolymerizing with polydimethylsiloxane has an average number of ethylene oxide repeating units of 5 to 30, preferably 5 to 25, in particular 10 to 20 or 7 to 20.

Suitable emulsifiers based on polysiloxane may be selected from the group consisting of dimethicone PEG-7 Phosphate, dimethicone PEG-10 Phosphate, dimethicone PEG/PPG-7/4 Phosphate, dimethicone PEG/PPG-12/4 Phosphate, PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 v, PEG/PPG-20/6 dimethicone, PEG/PPG-20/15 dimethicone, PEG/PPG-20/20 dimethicone, PEG/PPG-20/29 dimethicone, PEG/PPG-22/23 dimethicone, PEG/PPG-22/24 dimethicone, PEG/PPG-25/25 dimethicone, PEG/PPG-27/27 dimethicone Surfactant—solubilizing agent—PEG/PPG-20/23 dimethicone, PEG/PPG-23/6 dimethicone. It is a preferred embodiment according to the invention, that the emulsifier is based on polysiloxanes selected from the group consisting of PEG-12 dimethicone crosspolymer, PEG-10 dimethicone, PEG-12 dimethicone, PEG/PPG-18/18 dimethicone, PEG/PPG-19/19 dimethicone, bis-isobutyl PEG/PPG-18/18 dimethicone copolymer, and mixtures thereof, in particular PEG-12 dimethicone crosspolymer, PEG-12 dimethicone, PEG/PPG-18/18 dimethicone, PEG/PPG-19/19 dimethicone, and mixtures thereof.

In a preferred embodiment, the emulsifier according to the present invention is based on a mixture of PEG-12 dimethicone and PEG/PPG-19/19 dimethicone. In yet another preferred embodiment, the emulsifier according to the present invention is PEG-12 dimethicone.

The emulsifier according to the present invention is preferably based on polysiloxane and is used as a dispersion, containing 1 to 95% by weight of a solvent.

The emulsifier according to the present invention is preferably based on polysiloxane and is used as a dispersion, comprising a solvent selected from the group consisting of cyclopentasiloxane, dimethicone, and a mixture of C13-16 isoparaffin and C10-13 isoparaffin.

In a particular embodiment of the present invention, the emulsifier is based on PEG-12 dimethicone crosspolymer and is used as a dispersion, containing 85 to 90% by weight of cyclopentasiloxane, based on PEG/PPG-18/18 dimethicone and is used as a dispersion, containing 85 to 90% by weight of cyclopentasiloxane, based on PEG/PPG-19/19 dimethicone and is used as dispersion, containing 40 to 60% by weight of cyclopentasiloxane, or based on a mixture of PEG-12 dimethicone and PEG/PPG-19/19 dimethicone and wherein PEG/PPG-19/19 dimethicone is used as a dispersion, containing 40 to 60% by weight of cyclopentasiloxane.

If the emulsifier according to the present invention is based on a mixture of PEG-12 dimethicone and PEG/PPG-19/19 dimethicone and wherein PEG/PPG-19/19 dimethicone is used as a dispersion, containing 40 to 60% by weight of cyclopentasiloxane, the weight ratio of the PEG-12 dimethicone and the PEG/PPG-19/19 dimethicone dispersion is 0.5:1 to 1:5, preferably 1:1 to 1:3, in particular 1:1.1 to 1:2.3.

In another certain embodiment of the present invention, the emulsifier is based on polyisobutylene. Preferably, the emulsifier according to the present invention is a hydrophilic emulsifier based on polyisobutylene.

It is preferred that the emulsifier based on polyisobutylene comprises at least one polyisobutylene linked to a succinic acid derivative. Preferably, the polyisobutylene has a number average molecular weight of Mn=300 to 10,000. Emulsifier based on polyisobutylene comprising at least one polyisobutylene linked to a succinic acid derivative are, for example, available under the product name LAKPOL (PIBSA), for example LAKPOL 1110 (PIBSA).

If the emulsifier based on polyisobutylene comprises at least one polyisobutylene linked to a succinic acid derivative, the succinic acid derivative is preferably linked to a hydrophilic compound comprising at least two polyethylene glycols having an average number of ethylene oxide repeating units of 1 to 50, or of 1 to 10.

In another certain embodiment of the present invention, the emulsifier is based on ethoxylated castor oil. Suitable ethoxylated castor oil are selected from the group consisting of polyoxyl castor oils with 20 to 50, preferably 30 to 40, oxyethylene units and polyoxyl hydrogenated castor oils with 30 to 70, preferably 35 to 60, oxyethylene units. Preferably, the ethoxylated castor oil is selected from the group consisting of polyoxyl 35 hydrogenated castor oil, polyoxyl 40 castor oil, polyoxyl 40 hydrogenated castor oil, polyoxyl 60 hydrogenated castor oil, and mixtures thereof. Preferably, the emulsifier is polyoxyl 35 hydrogenated castor oil.

In another certain embodiment of the present invention, the emulsifier is based on poloxamer. Poloxamers, also known as polyoxyethylene-propylene glycol copolymer and polyoxyethylene-polyoxypropylene copolymer, are known in the field of polymers with the commercial names of families of polyoxyethylene-polyoxypropylene-polyoxyethylene block polymers such as Lutrol®, Monolan®, Pluronic®, Supronic®, Synperonic®.

Preferably, the poloxamer is liquid at 20° C. In particular, the two polyethyle oxide blocks of the poloxamer have an ethylene oxide repeating units number of 12 and the propylene oxide block of the poloxamer has a propylene oxide repeating units number of 20.

In accordance with the invention, the commercially available poloxamers under the trade name Lutrol®, Monolan®, Pluronic®, Supronic®, Synperonic® are preferred, in particular, Lutrol® L44.

The emulsifier according to the present invention reduces the maximum size of the dispersed deposits in a biphasic coating mixture during the process of preparing a transdermal therapeutic system in accordance with the invention.

Further, the emulsifier according to the present invention reduces the maximum size of the dispersed deposits in the biphasic matrix layer of a transdermal therapeutic system in accordance with the invention.
Polymer The TTS according to the present invention comprises at least one polymer in the continuous, outer phase of the biphasic matrix layer.

Preferably, the at least one polymer in the continuous, outer phase is a hydrophobic polymer.

Preferred are polymers based on polysiloxanes, polyisobutylenes, or styrene-isoprene-styrene block copolymers. In certain embodiments of the present invention, the at least one polymer in the continuous, outer phase is polysiloxane or polyisobutylene.

In certain embodiments of the present invention, the at least one polymer in the continuous, outer phase is a pressure-sensitive adhesive polymer.

In certain embodiments of the present invention, the composition of the continuous, outer phase is a pressure-sensitive adhesive composition.

In certain embodiments of the invention, the polymer in the continuous, outer phase is a pressure-sensitive adhesive polymer selected from the group of polysiloxanes, polyisobutylenes, polyacrylates, copolymers of styrene and butadiene, copolymers of styrene and isoprene.

In a certain embodiment of the present invention, the at least one polymer in the continuous, outer phase is a pressure-sensitive adhesive polymer based on polysiloxane or polyisobutylene.

Pressure-sensitive adhesive polymers being suitable for a hot-melt coating exhibit a dynamic viscosity of no more than 60 Pa·s, no more than 80 Pa·s, no more than 100 Pa·s, no more than 120 Pa·s or at most 150 Pa·s at a temperature of 160° C. Depending on the dynamic viscosity of the pressure-sensitive adhesive polymer at 160° C., the addition of a softener, such as waxes, silicone oils, glycerin, condensates from glycerin with fatty acids or polyols, or laurylacetate, or, in particular, glycerolmonolaurate, laurylacetate, waxes of the formula R—C(O)—OR', alkylmethylsiloxane waxes, siloxated polyether waxes, organic waxes or glycerin, may be required to adjust the viscosity of the pressure-sensitive adhesive polymer(s) in a suitable manner during hot-melt manufacturing processes.

Pressure-sensitive adhesive polymers being suitable for solvent-containing coating mixtures exhibit a dynamic viscosity of above 150 Pa·s at a temperature of 160° C. and therefore require the addition of a softener in order to be suitable for a hot-melt manufacturing process.

The at least one polymer (e.g. the pressure-sensitive adhesive) is contained in the biphasic matrix layer and may further be contained in the additional adhesive overlay, if present.

Preferred pressure-sensitive adhesives are usually supplied and used in solvents like n-heptane and ethyl acetate. The solids content of the pressure-sensitive adhesives is usually between 30% and 80%.

Suitable polymers according to the invention are commercially available e.g. under the brand names Bio-PSAs (polysiloxanes), Oppanol™ (polyisobutylenes), or JSR-SIS (a styrene-isoprene-styrene copolymer).

Pressure-sensitive adhesives based on polysiloxanes may also be referred to as silicone-based pressure-sensitive adhesives, or silicone pressure-sensitive adhesives. Pressure-sensitive adhesives based on polysiloxanes may have a solids content preferably between 60% and 80%.

Such silicone-based PSAs need, unlike other organic pressure sensitive adhesives, no additives like antioxidants, stabilizers, plasticizers, catalysts or other potentially extractable ingredients. These pressure-sensitive adhesives provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The silanol end blocked polydimethylsiloxane content contributes to the viscous component of the visco-elastic behavior, and impacts the wetting and the spreadability properties of the adhesive. The resin acts as a tackifying and reinforcing agent, and participates in the elastic component. The correct balance between silanol end blocked polydimethylsiloxane and resin provides for the correct adhesive properties.

Examples of silicone-based PSA compositions which are commercially available include the standard BIO-PSA series (7-4400,7-4500 and 7-4600 series) and the amine compatible (endcapped) BIO-PSA series (7-4100, 7-4200 and 7-4300 series) manufactured and typically supplied in n-heptane or ethyl acetate by Dow Corning. For example, BIO-PSA 7-4201 is characterized by a solution viscosity at 25° C. and about 60% solids content in heptane of 450 mPa s and a complex viscosity at 0.01 rad/s at 30° C. of $1\times10^8$ Poise. BIO-PSA 7-4301 has a solution viscosity at 25° C. and about 60% solids content in heptane of 500 mPa s and a complex viscosity at 0.01 rad/s at 30° C. of $5\times10^6$ Poise.

The polysiloxanes are supplied and used in solvents like n-heptane, ethyl acetate or other volatile silicone fluids. For the present invention n-heptane is preferred. The solids content of polysiloxanes in solvents is usually between 60 and 85%, preferably between 70 and 80%. The skilled person is aware that the solids content may be modified by adding a suitable amount of solvent.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s. Theses may also be characterized by a complex viscosity at 0.01 rad/s at 30° C. of less than about $1\times10^9$ Poise or from about $1\times10^5$ to about $9\times10^8$ Poise, preferably as measured using a Brookfield RVT viscometer equipped with a spindle number 5 at 50 rpm.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. A preferred example for a polyisobutylene combination is B10/B100 in a ratio of 85/15. Oppanol® B100 has a viscosity average molecular weight $M_v$ of 1,110,000, and a weight average molecular weight $M_w$ of 1,550,000, and an average molecular weight distribution $M_w/M_n$ of 2.9. Oppanol® B10 has a viscosity average molecular weight $M_v$ of 40,000, and a weight average molecular weight $M_w$ of 53,000, and an average molecular weight distribution $M_w/M_n$ of 3.2. In certain embodiments, polybutene may be added to the polyisobutylenes. The solids content of polyisobutylenes in solvents is usually between 30 and 70%, preferably between 35 and 65%. The skilled person is aware that the solids content may be modified by adding a suitable amount of solvent.

Active Agent

The active agent can be any component suitable for transdermal delivery to a patient. Suitable active agent include, but are not limited to, buprenorphine and diclofenac.

In a certain embodiment according to the present invention, the active agent is an active agent suitable for the systemic treatment, i.e. active agents for administration to the systemic circulation.

In another certain embodiment according to the present invention, the active agent is an active agent suitable for the local treatment, i.e. active agents for topical administration to the local areas to be treated.

In accordance with the present invention, the active agent may be present in the TTS in any form as defined above.

Thus, in certain embodiments, the active in the biphasic matrix layer may be included in the form of the free base.

In other certain embodiments, the active in the biphasic matrix layer may be included in the form of a pharmaceutically acceptable chemical and morphological form and physical state, such as a pharmaceutically acceptable salt thereof.

In certain embodiments, the biphasic matrix layer is obtainable by incorporating the active agent in the form of the free base. In a further embodiment, the biphasic matrix layer is obtainable by incorporating the active agent in the form of a pharmaceutically acceptable salt thereof.

To a large extent, the active agent is not dissolved within the polymer of the continuous, outer phase but within the discontinuous, inner phase, which forms the microreservoirs incorporated within the polymer of the continuous, outer phase.

The amount of the active agent incorporated into the system varies depending on many factors including, but not limited to, the particular active agent, the desired therapeutic effect, and the time span for which the system is to provide therapy. For most active agents, the passage of the active agent through the skin is the rate-limiting step in transdermal delivery. Thus, the amount of the active agent and the rate of release are typically selected so as to provide transdermal delivery characterized by a zero order time dependency for a prolonged period of time. The minimum amount of active agent in the system is selected based on the amount of active agent which passes through the skin, or other substrate, in the time span for which the system is to provide therapy.

In a preferred embodiment of the present invention, the active agent is contained in the transdermal therapeutic system in an amount of from 1 to 50 mg.

In yet another preferred embodiment of the present invention, the active agent is contained in an amount of from 1 to 30%, preferably from 1 to 15%, more preferably from 2 to 12% by weight based on the biphasic matrix layer.

In yet another preferred embodiment of the present invention, the active agent is contained in an amount of from 0.1 to 5 mg/cm², preferably from 0.5 to 1.5 mg/cm², or from 3 to 5 mg/cm² based on the biphasic matrix layer.

In a certain embodiment according to the present invention, the active agent is selected from the group consisting of buprenorphine and diclofenac.

In a certain embodiment according to the present invention, the active agent is buprenorphine base, wherein the buprenorphine-containing layer is preferably obtainable by incorporating the buprenorphine in the form of the free base.

In the event that buprenorphine base is the active agent, buprenorphine base is contained in an amount of from 1 to 15%, preferably from 8 to 12% or from 5 to 7% by weight of the biphasic matrix layer.

In a certain embodiment according to the present invention, the active agent is diclofenac sodium. In the event that diclofenac sodium is the active agent, diclofenac sodium is contained in an amount of from 1 to 15%, preferably from 2 to 8%, more preferably from 3 to 5%, by weight of the biphasic matrix layer.

In a particular embodiment of the present invention, the active agent is buprenorphine, the at least one polymer is a pressure-sensitive adhesive based on polysiloxane or polyisobutylene, the emulsifier is based on polysiloxane, and the biphasic matrix layer further contains levulinic acid, and wherein preferably the levulinic acid and the buprenorphine are contained in the transdermal therapeutic system in an amount ratio of from 0.5:1 to 2:1.

In another particular embodiment of the present invention, the active agent is diclofenac, the at least one polymer is a pressure-sensitive adhesive based on polysiloxane or polyisobutylene, the emulsifier is based on polysiloxane, and the biphasic matrix layer further contains oleic acid, and wherein preferably the oleic acid and the diclofenac are contained in the transdermal therapeutic system in an amount ratio of from 2:1 to 5:1.

Method of Manufacture

According to one aspect, the invention relates to a method of stabilizing a biphasic coating mixture that comprises a discontinuous, inner phase having a composition comprising the active agent and a dissolver (e.g. carboxylic acid) for the active agent in amount sufficient so that the active agent forms a solution with the dissolver in the inner phase, the inner phase for mixing dispersed deposits in a continuous, outer phase comprising a polymer, by mixing the biphasic coating mixture with an emulsifier that is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

According to one further aspect, the invention relates to a stabilized biphasic coating mixture obtainable by the above described process, wherein the dispersed deposits in the biphasic coating mixture have a maximum droplet size of less than 55 μm.

The invention further relates to a method for manufacture of a biphasic matrix layer comprises the steps of:
(1) preparing a stabilized biphasic coating mixture in accordance with the present invention,
(2) coating the stabilized biphasic coating mixture on a film in an amount to provide the desired area weight,
(3) evaporating the solvents to provide a biphasic matrix layer with the desired area weight.

The invention further relates to a method for manufacturing a transdermal therapeutic system comprising the steps of:
(1) providing a stabilized biphasic coating mixture comprising
   a. a polymer (e.g. polysiloxane or polyisobutylene),
   b. an active agent (e.g. buprenorphine or diclofenac)
   c. a dissolver for the active agent (e.g. levulinic acid or oleic acid),
   d. an emulsifier (e.g. an emulsifier based on polysiloxane or polyisobutylene),
   e. a solvent (e.g. n-heptane and ethanol or n-hexane and methanol),
   f. optionally a viscosity-increasing substance (e.g. polyvinylpyrrolidone) and/or further excipients or additives,
(2) coating the stabilized biphasic coating mixture on a film in an amount to provide the desired area weight,
(3) evaporating the solvents to provide a biphasic matrix layer with the desired area weight,
(4) laminating the biphasic matrix layer to a backing layer to provide an active agent-containing layer structure,
(5) optionally laminating the active agent-containing layer structure to an additional skin contact layer,
(6) optionally punching the individual systems from the buprenorphine-containing self-adhesive layer structure with the desired area of release, and
(7) optionally adhering to the individual systems an active-free self-adhesive layer structure comprising also a backing layer and an active agent-free pressure-sensitive adhesive layer and which is larger than the individual systems of buprenorphine-containing self-adhesive layer structure.

According to a certain preferred embodiment of the present invention, in step 1 of said method of manufacture levulinic acid is used as dissolver for buprenorphine, the two are dissolved in ethanol and subsequently suspended in a pressure-sensitive adhesive based on polysiloxane in heptane to provide a buprenorphine-containing biphasic mixture.

According to a certain other preferred embodiment of the present invention, in step 1 of said method of manufacture oleic acid is used as a dissolver for diclofenac, the two are dissolved in methanol and subsequently suspended in a pressure-sensitive adhesive based on polysiloxane in heptane or a pressure-sensitive adhesive based on polyisobutylene in hexane to provide a diclofenac-containing biphasic mixture.

Release Characteristics

The TTS in accordance with the invention is be designed for transdermally administering an active agent to the local area to be treated or to the systemic circulation for a predefined extended period of time, preferably for 24, 84, or 168 hours.

Whether the skin permeation rate of the active agent is sufficient for a therapeutic effect can be determined by comparing the Franz diffusion cell skin permeation rates of a reference TTS including the same active agent with the Franz diffusion cell skin permeation rates of the TTS in accordance with the invention.

According to one embodiment, the TTS in accordance with one specific aspect of the invention containing buprenorphine as active agent provides a skin permeation rate of buprenorphine when measured in a comparable test with a commercial buprenorphine reference transdermal therapeutic system (e.g. BuTrans®) in a 72-hour time interval from hour 96 to hour 168 that is therapeutically effective.

According to one specific embodiment, the TTS in accordance with one specific aspect of the invention containing buprenorphine as active agent, provides a skin permeation rate of buprenorphine when measured in a comparable test with a commercial buprenorphine reference transdermal therapeutic system (e.g. BuTrans®) in a 96-hour time interval from hour 72 to hour 168 is provided that is therapeutically effective. Preferably, a skin permeation rate of buprenorphine when measured in a comparable test with a commercial buprenorphine reference transdermal therapeutic system in a 160-hour time interval from hour 8 to hour 168 is provided that is therapeutically effective.

According to one embodiment, the TTS in accordance with one specific aspect of the invention containing buprenophine as active agent, provides a therapeutically effective amount of buprenophine for about 168 hours during an administration period on the skin of a human patient of about 168 hours.

According to one embodiment, the TTS in accordance with one specific aspect of the invention containing diclofenac as active agent, provides a skin permeation rate of diclofenac when measured in a comparable test with a commercial diclofenac reference transdermal therapeutic system (e.g. Voltaren® Patch) in a 16-hour time interval from hour 8 to hour 24 that is therapeutically effective.

According to one embodiment, the TTS in accordance with one specific aspect of the invention containing diclofenac as active agent, provides a skin permeation rate of diclofenac when measured in a comparable test with a commercial diclofenac reference transdermal therapeutic system (e.g. Voltaren® Patch) in a 40-hour time interval from hour 8 to hour 48 that is therapeutically effective.

According to one embodiment, the TTS in accordance with one specific aspect of the invention containing diclofenac as active agent, provides a skin permeation rate of diclofenac when measured in a comparable test with a commercial diclofenac reference transdermal therapeutic system (e.g. Voltaren® Patch) in a 64-hour time interval from hour 8 to hour 72 that is therapeutically effective.

According to one embodiment, the TTS in accordance with one specific aspect of the invention containing diclofenac as active agent, provides a therapeutically effective amount of diclofenac for about 24 hours during an administration period on the skin of a human patient of about 24 hours.

According to one embodiment, the TTS in accordance with one specific aspect of the invention containing diclofenac as active agent, provides a therapeutically effective amount of diclofenac for about 72 hours during an administration period on the skin of a human patient of about 72 hours.

Method of Treatment/Medical Use

According to certain embodiments of the invention, therapeutically effective amounts of the active agent (e.g. buprenorphine or diclofenac) are provided for 1 to 7 days (24 to 168 hours) by said transdermal therapeutic system during an administration period of 1 to 7 days (24 to 168 hours).

A TTS according to the invention has the advantage of allowing for a more constant administration of the active agent during the administration period.

According to one aspect, the TTS in accordance with one specific aspect of the invention containing buprenorphine as active agent and as described above in detail is for use in a method of treatment, in particular for use in a method of treating pain.

The method comprises in particular the application of the TTS for 7 days (168 hours) on the skin of a human patient. According to certain other methods in accordance with the invention the TTS can be applied for at least 1 day, or 3 days, or 3.5 days, or 4 days, or 7 days on the skin of a human patient.

The TTS according to the invention is in particular for use in a method of treatment wherein the TTS is applied for 7 days on the skin of a human patient. According to certain aspects of the present invention the TTS is for use in a method of treatment wherein the TTS is applied for at least 1 day, or 3 days, or 3.5 days, or 4 days, or 7 days on the skin of a human patient.

In a certain embodiment, the TTS according to the invention, wherein the active agent is buprenorphine, is for use in a method of treating pain wherein the transdermal therapeutic system is applied for at least 3.5 days on the skin of a patient.

In a preferred embodiment, the TTS according to the invention wherein the active agent is buprenorphine, is for use in a method of treating pain wherein the transdermal therapeutic system is applied for 7 days on the skin of a patient.

According to one aspect, the TTS in accordance with one specific aspect of the invention containing diclofenac as active agent and as described above in detail is for use in a method of treating patients suffering from pain/inflammation such as osteoarthritis, shoulder periarthritis, muscle pain, low back pain, rheumatism, bruises, pulled muscles, lumbago, arthrosis, sweat gland abscess, or Multiple system atrophy.

The method comprises in particular the application of the TTS for 1 day (24 hours) on the skin of a human patient. According to certain other methods in accordance with the invention the TTS can be applied for at least 1.5 days, or 2 days, or 3 days on the skin of a human patient.

The TTS according to the invention is in particular for use in a method of treatment wherein the TTS is applied for 1 day on the skin of a human patient. According to certain aspects of the present invention the TTS is for use in a method of treatment wherein the TTS is applied for at least 1.5 days, or 2 days, or 3 days on the skin of a human patient.

In a certain embodiment, the TTS according to the invention, wherein the active agent is diclofenac, is for use in a method of treating patients suffering from pain/inflammation such as osteoarthritis, shoulder periarthritis, muscle pain, low back pain, rheumatism, bruises, pulled muscles, lumbago, arthrosis, sweat gland abscess, or Multiple system wherein the transdermal therapeutic system is applied for 1 day on the skin of a patient.

In a certain embodiment, the TTS according to the invention, wherein the active agent is diclofenac, is for use in a method of treating patients suffering from pain/inflammation such as osteoarthritis, shoulder periarthritis, muscle pain, low back pain, rheumatism, bruises, pulled muscles, lumbago, arthrosis, sweat gland abscess, or Multiple system wherein the transdermal therapeutic system is applied for 3 days on the skin of a patient.

EXAMPLES

The present invention will now be more fully described with reference to the accompanying examples. It should be understood, however, that the following description is illustrative only and should not be taken in any way as a restriction of the invention.

Comparative Example 1

The composition of a diclofenac sodium-containing adhesive coating mixture is summarized in Table 1 below.

TABLE 1

| Ingredient (Trade Name) | Amt/unit (g) |
| --- | --- |
| Diclofenac sodium | 3.3 |
| Oleic acid | 9.9 |
| Methanol | 9.9 |
| Polyisobutylene/polybutylene adhesive in n-hexane Solids content of 60% by weight (PIB B10/B100 (85%/15%) from BASF SE) | 124.7 |
| gasoline | 32.8 |
| Total | 180.6 |

In a suitable vessel, e.g. a stainless steel or glass vessel, 3.3 g of diclofenac sodium were dissolved in 9.9 g of methanol. Subsequently, 9.9 g of oleic acid were added and the mixture was stirred until homogenous. 124.7 g of a polyisobutylene/polybutylene adhesive in the form of a solution in n-hexane having a solids content of 60% by weight and 32.8 g of gasoline were added. The mixture was stirred to give 180.6 g of a diclofenac-containing adhesive mixture with 1.8% by weight of diclofenac sodium, with a solids content of 48.5%.

The diclofenac-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 3.75% by weight of diclofenac sodium and 11.25% by weight of oleic acid in this matrix layer. The biphasic matrix layer can then be laminated with a backing layer.

Figure 1B:
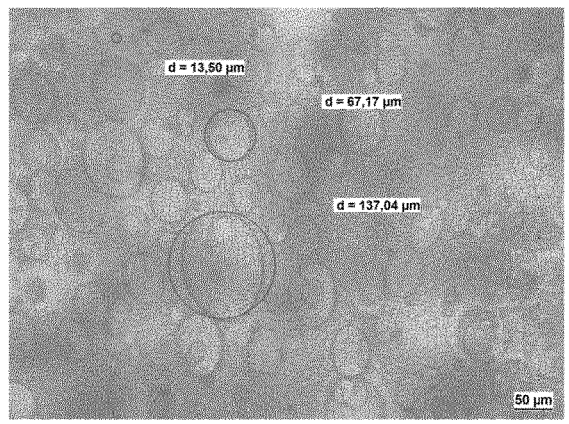
FIG. 1B depicts the diclofenac-containing biphasic matrix layer of Comparative Example 1.

Microscopic pictures were taken of the diclofenac sodium-containing adhesive coating mixture and the matrix layer using a Nikon S/N 237789 Microscope. FIG. 1A shows a microscopic picture of the diclofenac sodium-containing adhesive coating mixture of Comparative example 1 and FIG. 1B shows a microscopic picture of the matrix layer of Comparative example 1. During the microscopic investigation the droplet size (diameter) in the coating mixture and the size of the spheres (diameter) in the matrix layer were determined. FIG. 1B shows numerous spheres which are larger than 50 µm in the dried matrix layer due to the coalescence which occurred during the coating procedure. The maximum droplet sizes in the coating mixture and the maximum sphere size in the matrix layer are summarized in Table 2 below.

TABLE 2

| Comparative example 1 | |
| --- | --- |
| Maximum droplet size coating mixture (FIG. 1A) | Maximum sphere size matrix layer (FIG. 1B) |
| 106 µm | 137 µm |

Comparative Example 2

The composition of a diclofenac sodium-containing adhesive coating mixture is summarized in Table 3 below.

TABLE 3

| Ingredient (Trade Name) | Amt/unit (g) |
| --- | --- |
| Diclofenac sodium | 4.9 |
| Oleic acid | 14.6 |
| Methanol | 14.6 |
| Polysiloxane adhesive in n-heptane Solids content of 73% by weight (BIO-PSA 7-4201 from Dow Corning Healthcare) | 151.4 |
| Total | 185.5 |

In a suitable vessel, e.g. a stainless steel or glass vessel, 4.9 g of diclofenac sodium were dissolved in 14.6 g of methanol. Subsequently, 14.6 g of oleic acid were added and the mixture was stirred until homogenous. 151.4 g of a polysiloxane adhesive in the form of a solution in n-heptane having a solids content of 73% by weight were added. The mixture was stirred to give 185.5 g of a diclofenac-containing adhesive mixture with 2.6% by weight of diclofenac sodium, with a solids content of 70.1%.

The diclofenac-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 3.75% by weight of diclofenac sodium and 11.25% by weight of oleic acid in this matrix layer. The biphasic matrix layer can then be laminated with a backing layer.

Figure 2A:
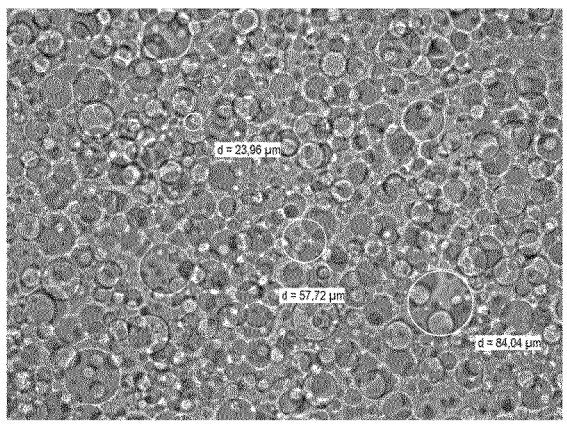
FIG. 2A depicts the diclofenac-containing biphasic coating mixture of Comparative Example 2.
Figure 2B:
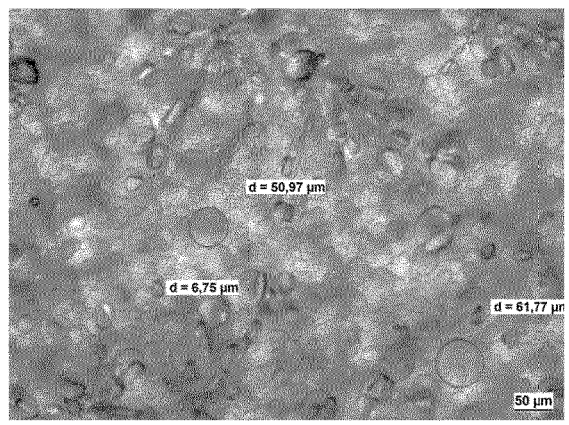
FIG. 2B depicts the diclofenac-containing biphasic matrix layer of Comparative Example 2.

Microscopic pictures were taken of the diclofenac sodium-containing adhesive coating mixture and the matrix layer using a Nikon S/N 237789 Microscope. FIG. 2A shows a microscopic picture of the diclofenac sodium-containing adhesive coating mixture of Comparative Example 2 and FIG. 2B shows a microscopic picture of the matrix layer of Comparative Example 2. During the microscopic investigation the droplet size (diameter) in the matrix layer and the size of the spheres (diameter) in the matrix layer were determined. FIG. 2B shows numerous spheres which are larger than 30 µm in the dried matrix layer and also crystallized diclofenac-sodium. The maximum droplet sizes in the coating mixture and the maximum sphere size in the matrix layer are summarized in Table 4 below.

TABLE 4

| Comparative example 2 | |
| --- | --- |
| Maximum droplet size coating mixture (FIG. 2A) | Maximum sphere size matrix layer (FIG. 2B) |
| 84 µm | 62 µm |

Example 1

The composition of a diclofenac sodium-containing adhesive coating mixture is summarized in Table 5 below.

TABLE 5

| Ingredient (Trade Name) | Amt/unit (g) |
| --- | --- |
| Diclofenac sodium | 3.2 |
| Oleic acid | 9.7 |
| Methanol | 9.7 |
| Cyclopentasiloxane (and) PEG-12 dimethicone crosspolymer (DC 9011 from Dow Corning Healthcare) | 2.6 |
| Polyisobutylene/polybutylene adhesive in n-hexane Solids content of 60% by weight (PIB B10/B100 (85%/15%) from BASF SE) | 117.5 |
| Gasoline | 34.1 |
| Total | 176.8 |

In a suitable vessel, e.g. a stainless steel or glass vessel, 3.2 g of diclofenac sodium were dissolved in 9.7 g of methanol. Subsequently, 9.7 g of oleic acid were added. Cyclopentasiloxane (and) PEG-12 dimethicone crosspolymer was added and the mixture was stirred until homogenous. Polyisobutylene/polybutylene adhesive in n-hexane having a solids content of 60% by weight were added followed by 34.1 g of Gasoline. The mixture was stirred to give 176.8 g of a diclofenac-containing adhesive mixture with 1.8% by weight of diclofenac sodium, with a solids content of 48.6%.

The diclofenac-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m². This results in 3.75% by weight of diclofenac sodium and 11.25% by weight of oleic acid in this matrix layer.

The biphasic matrix layer was laminated with the backing layer to provide the diclofenac sodium-containing layer structure.

The individual systems (TTS) were then punched from the diclofenac sodium-containing layer structure.

In specific embodiments a TTS as described above can be provided with an adhesive overlay. The overlay is laminated onto the punched or cut individual systems which are then punched out by only punching the overlay and sealed into pouches of the primary packaging material.

Figure 3A:
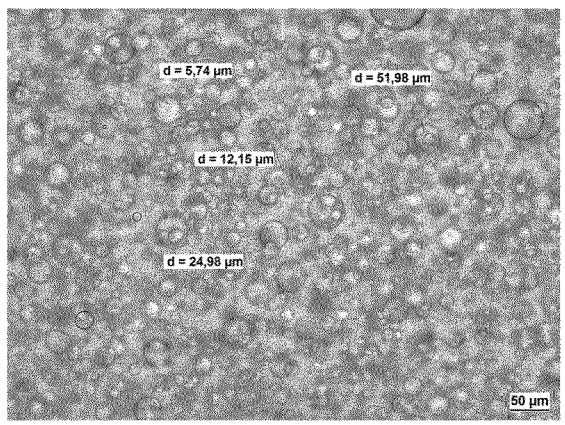
FIG. 3A depicts the diclofenac-containing biphasic coating mixture of Example 1.
Figure 3B:
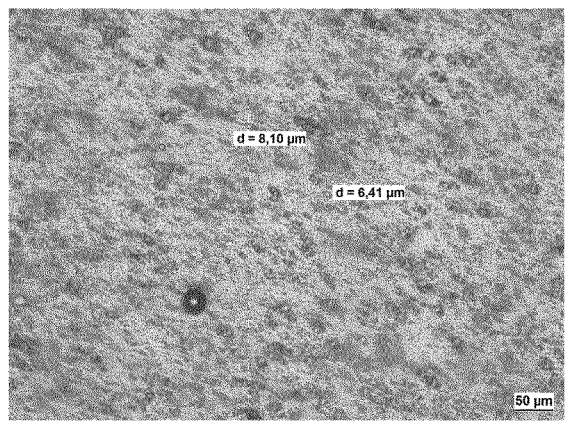
FIG. 3B depicts the diclofenac-containing biphasic matrix layer of Example 1.

Microscopic were taken of the diclofenac sodium-containing adhesive coating mixture and the matrix layer using a Nikon S/N 237789 Microscope. FIG. 3A shows a microscopic picture of the diclofenac-containing adhesive coating mixture of Example 1 and FIG. 3B shows a microscopic picture of the matrix layer of Example 1. During the microscopic investigation the droplet size (diameter) in the coating mixture and the size of the spheres (diameter) in the matrix layer were determined. FIG. 3B shows that in the dried matrix layer an enlargement of spheres has not taken place. The maximum droplet sizes in the coating mixture and the maximum sphere size in the matrix layer are summarized in Table 6 below.

TABLE 6

| Example 1 | |
| --- | --- |
| Maximum droplet size coating mixture (FIG. 3A) | Maximum sphere size matrix layer (FIG. 3B) |
| 52 μm | 8 μm |

Example 2

The composition of a diclofenac sodium-containing adhesive coating mixture is summarized in Table 7 below.

TABLE 7

| Ingredient (Trade Name) | Amt/unit (g) |
| --- | --- |
| Diclofenac sodium | 4.8 |
| Oleic acid | 14.3 |
| Methanol | 14.3 |
| PEG-12 Dimethicon (DC 5329 from Dow Corning Healthcare) | 1.6 |
| Cyclopentasiloxan/PEG/PPG-19/19 Dimethicon (DC BY 11-030 from Dow Corning Healthcare) | 3.5 |
| Polysiloxane adhesive in n-heptane Solids content of 73% by weight (BIO-PSA 7-4201 from Dow Corning Healthcare) | 140.9 |
| Total | 179.4 |

In a suitable vessel, e.g. a stainless steel or glass vessel, 4.8 g of diclofenac sodium was dissolved in 4.5 g ethanol. Subsequently, 14.3 g of oleic acid, 1.6 g PEG-12 Dimethicon and 3.5 g Cyclopentasiloxan/PEG/PPG-19/19 Dimethicon were added and the mixture was stirred until homogenous. 140.9 g of a polysiloxane adhesive in the form of a solution in n-heptane having a solids content of 72.3% by weight were added. The mixture was stirred until homogeneous to give 179.4 g of a diclofenac-containing adhesive mixture with 2.7% by weight of diclofenac sodium, with a solids content of 70.8%.

The diclofenac-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m². This results in 3.75% by weight of diclofenac sodium, 11.25% by weight of oleic acid, 1.25% by weight of PEG-12 Dimethicon and 2.75% by weight of Cyclopentasiloxan/PEG/PPG-19/19 Dimethicon in this matrix layer.

The biphasic matrix layer was laminated with the backing layer to provide the diclofenac sodium-containing layer structure.

The individual systems (TTS) were then punched from the diclofenac sodium-containing layer structure.

In specific embodiments a TTS as described above can be provided with an adhesive overlay. The overlay is laminated onto the punched or cut individual systems which are then punched out by only punching the overlay and sealed into pouches of the primary packaging material.

Figure 4A:
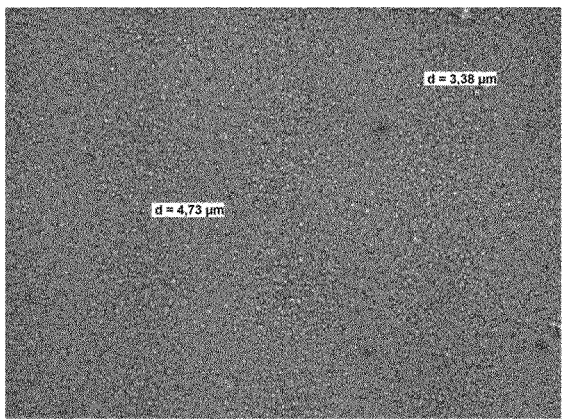
FIG. 4A depicts the diclofenac-containing biphasic coating mixture of Example 2.
Figure 4B:
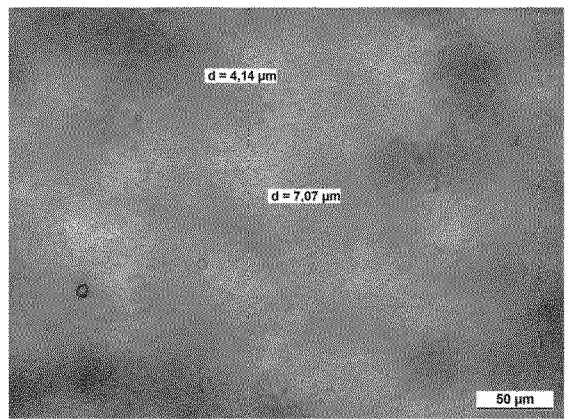
FIG. 4B depicts the diclofenac-containing biphasic matrix layer of Example 2.

Microscopic pictures were taken of the diclofenac sodium-containing adhesive coating mixture and the matrix layer using a Nikon S/N 237789 Microscope. FIG. 4A shows a microscopic picture of the diclofenac sodium-containing adhesive coating mixture of Example 2 and FIG. 4B shows a microscopic picture of the matrix layer of Example 2. During the microscopic investigation the droplet size (diameter) in the coating mixture and the size of the spheres (diameter) in the matrix layer were determined. FIG. 4B shows that in the dried matrix layer an enlargement of spheres has not taken place. The maximum droplet sizes in the coating mixture and the maximum sphere size in the matrix layer are summarized in Table 8 below.

TABLE 8

| Example 2 | |
| --- | --- |
| Maximum droplet size coating mixture (FIG. 4A) | Maximum sphere size matrix layer (FIG. 4B) |
| 5 μm | 7 μm |

Example 3

Figure 5A:
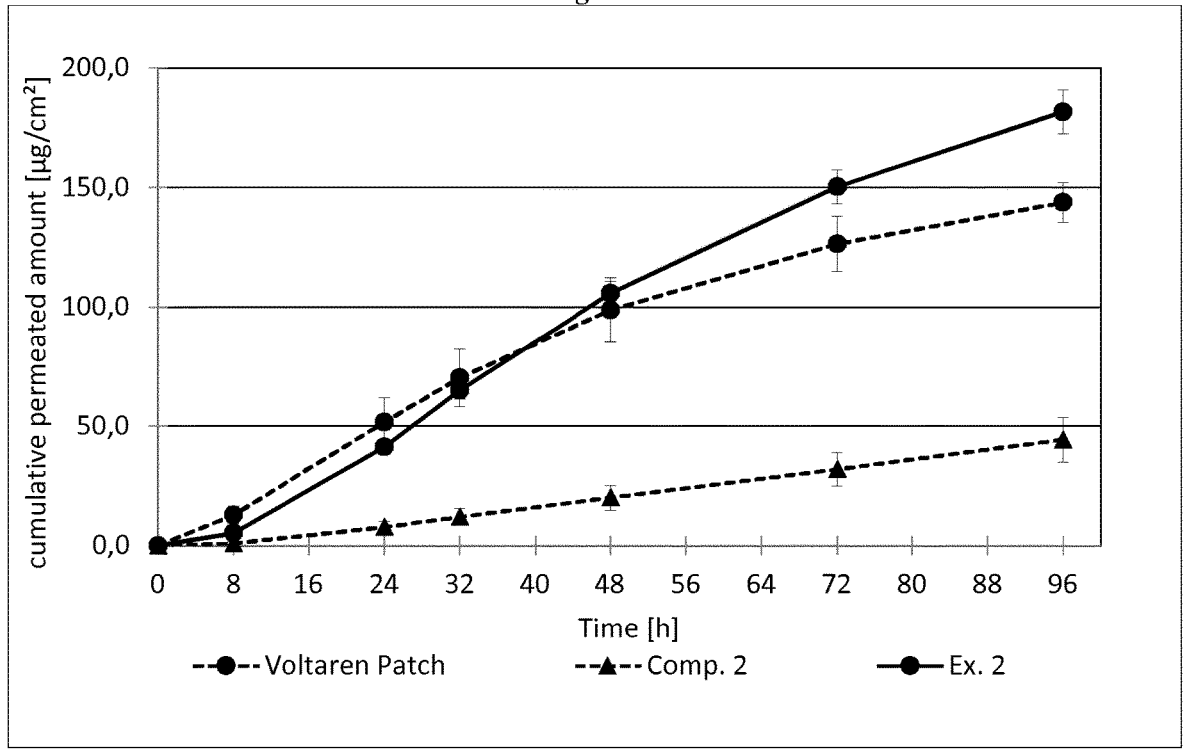
FIG. 5A depicts the cumulative permeated amount of Voltaren® Patch, Comparative Example 2, and Example 2 over a time interval of 96 hours.
Figure 5B:
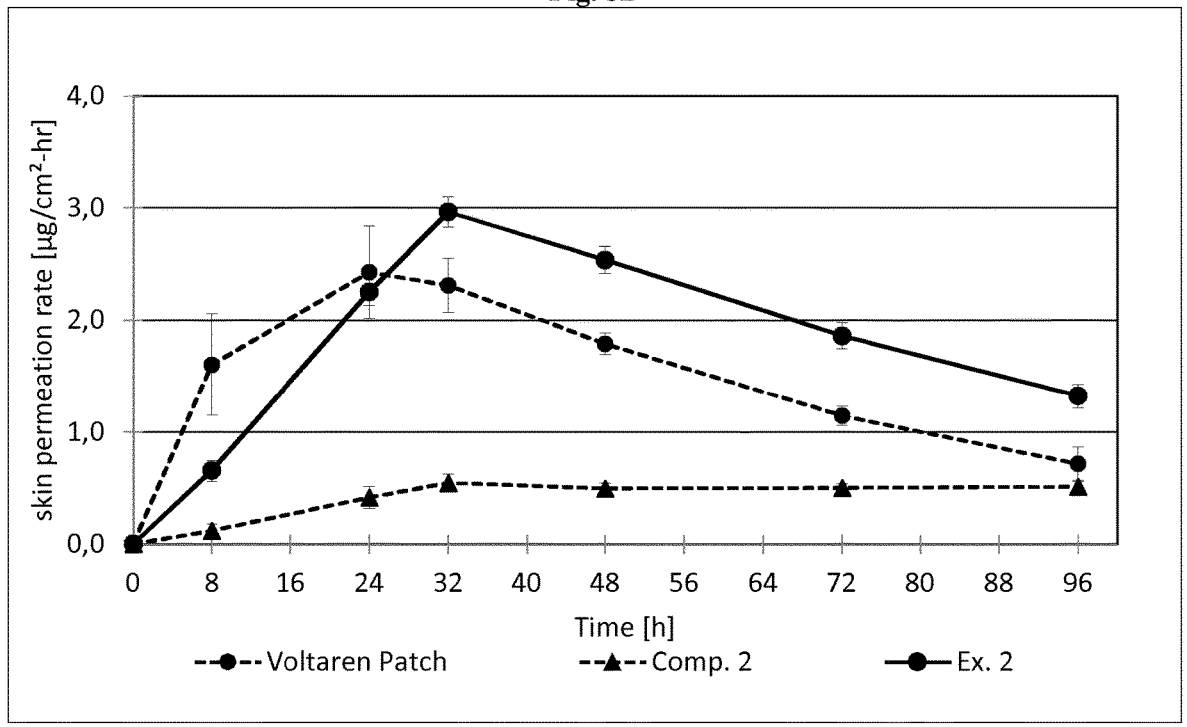
FIG. 5B depicts the skin permeation rate of Voltaren® Patch, Comparative Example 2, and Example 2 over a time interval of 96 hours.

In Example 3, the in vitro skin permeations of Comparative example 2, Example 2, and Voltaren® Patch 30 mg, manufactured by Dojin Iyaku-Kako Co., Ltd., were determined by in vitro experiments in accordance with the OECD Guideline (adopted Apr. 13, 2004) carried out with the Franz diffusion cell (a 9 ml Franz diffusion cell). Split thickness human skin from cosmetic surgeries (female abdomen, date of birth 1961 was used. A dermatome was used to prepare skin to a thickness of 500 μm, with an intact epidermis. Due to the prolonged test (96 hours) 500 μm skin is used instead of the recommended 200 to 400 μm skin. The receptor medium used is a phosphate buffer solution pH 5.5 with 0.1% saline azide as antibacteriological agent is used at a temperature of 32±1° C. Die cuts with an area of 1.156 cm² were punched from Comparative example 2 and were tested against 1.156 cm² die cuts of the commercial product Voltaren® Patch. The concentrations of diclofenac sodium in the receptor medium of the Franz cell at a temperature of 32±1° C. were measured. The results are shown in Tables 9 to 11 and FIGS. 5A and 5B.

TABLE 9

Cumulative permeated amount after certain elapsed time
[μg/cm²] n = 3 (RSD in %)

| Elapsed time (hr) | Comparative example 2 | Example 2 | Voltaren ® Patch |
|---|---|---|---|
| 0 | 0 | 0 | 0 |
| 8 | 0.974 (47) | 5.23 (14) | 12.8 (28) |
| 24 | 7.65 (26) | 41.3 (6) | 51.6 (20) |
| 32 | 12.0 (22) | 65.0 (5) | 70.1 (17) |
| 48 | 19.9 (17) | 106 (5) | 98.7 (14) |
| 72 | 32.0 (13) | 150 (5) | 126 (9) |
| 96 | 44.3 (12) | 182 (5) | 143 (6) |

TABLE 10

Permeated amount [μg/cm²] n = 3 (RSD in %)

| Elapsed time (hr) | Comparative example 2 | Example 2 | Voltaren ® Patch |
|---|---|---|---|
| 0 | 0 | 0 | 0 |
| 8 | 0.974 (47) | 5.23 (14) | 12.8 (28) |
| 24 | 6.68 (23) | 36.0 (5) | 38.8 (17) |
| 32 | 4.37 (15) | 23.7 (5) | 18.5 (11) |
| 48 | 7.91 (10) | 40.6 (5) | 28.6 (5) |
| 72 | 12.0 (8) | 44.6 (6) | 27.5 (7) |
| 96 | 12.3 (9) | 31.7 (8) | 17.2 (21) |

TABLE 11

Skin permeation rate [μg/cm² × hr] n = 3 (SD)

| Elapsed time (hr) | Comparative example 2 | Example 2 | Voltaren ® Patch |
|---|---|---|---|
| 0 | 0 | 0 | 0 |
| 8 | 0.12 (0.06) | 0.65 (0.09) | 1.60 (0.45) |
| 24 | 0.42 (0.10) | 2.25 (0.12) | 2.43 (0.41) |
| 32 | 0.55 (0.008) | 2.96 (0.14) | 2.31 (0.24) |
| 48 | 0.49 (0.05) | 2.54 (0.12) | 1.79 (0.10) |
| 72 | 0.50 (0.04) | 1.86 (0.12) | 1.14 (0.08) |
| 96 | 0.51 (0.05) | 1.32 (0.10) | 0.72 (0.15) |

Comparative Example 3

The composition of the buprenorphine base-containing adhesive coating mixture is summarized in Table 12 below.

TABLE 12

| Ingredient (Trade Name) | Amt/unit (kg) |
|---|---|
| Buprenorphine base | 1.368 |
| Levulinic acid | 0.958 |
| Polyvinylpyrrolidone (25% PVP pre-solution) | 0.342 |
| Ascorbyl palmitate | 0.027 |
| Ethanol | 1.938 |
| Polysiloxane adhesive in n-heptane Solids content of 73% by weight (BIO-PSA 7-4201 from Dow Corning Healthcare) | 15.048 |
| n-heptane | 0.319 |
| Total | 20 |

In a 10 l vessel, 1.00 kg of polyvinylpyrrolidone and 3.00 kg of ethanol were dissolved to form a 25 PVP pre-solution. In a homogenizing/mixing vessel: Becomix Lab mixer RW 30 Ex, 1.368 kg of PVP pre-solution, 0.958 kg levulinic acid, 0.027 kg of Ascorbyl palmitate and the main part of 0.912 kg of Ethanol were suspended by stirring. The prescribed amount of buprenorphine was weighed and added to the homogenizing/mixing vessel followed by rinsing the weighing container used for buprenorphine with the remaining part of ethanol. The mixture was kept under stirring for at least 1 h until a buprenorphine containing solution was formed. 15.048 kg of a polysiloxane adhesive in the form of a solution in n-heptane having a solids content of 73% by weight and 0.319 kg of n-heptane were added to the mixing/homogenizing vessel The mixture was stirred for at least 2 h until a buprenorphine-containing adhesive mixture with 6.8% of buprenorphine, with a solids content of 68% (buprenorphine base-containing adhesive mixture) was formed. Afterwards, this mixture was homogenized using a rotor-stator device using homogenizing unit at approx. 2250 rpm.

Within 24 hours the buprenorphine base-containing adhesive mixture was coated on a polyethylene terephthalate foil (e.g. Scotchpak from 3M) using a pilot plant roll coater including a drying tunnel, several drying sections, an unwinding and laminating station. The solvent was removed by drying at approximately 30-50° C. The matrix layer remained within the drying tunnel at approx. 8 minutes. The coating thickness was chosen such that removal of the solvents results in an area weight of the matrix layer of 120 g/m². This results in the 10% by weight of buprenorphine base and 7% by weight of levulinic acid and 2.5% by weight of polyvinylpyrrolidone in this matrix layer. The dried film was laminated with the backing layer (e.g. polyethyleneterephthalate (PET) foil 19 μm) to provide the buprenorphine-containing self-adhesive layer structure.

The individual systems (TTS) were then punched from the buprenorphine-containing self-adhesive layer structure.

In specific embodiments a TTS as described above can be provided with a further self-adhesive layer of larger surface area, preferably with rounded corners, comprising a pressure-sensitive adhesive matrix layer which is free of active ingredient and has a preferably beige colored backing layer (overtape). This is of advantage when the TTS, on the basis of its physical properties alone, does not adhere sufficiently to the skin and/or when the buprenorphine-containing matrix layer, for the purpose of avoiding waste, has pronounced corners (square or rectangular shapes.

The overtape including the TTS are then punched out by only punching the overtape and sealed into pouches of the primary packaging material.

Figure 6A:
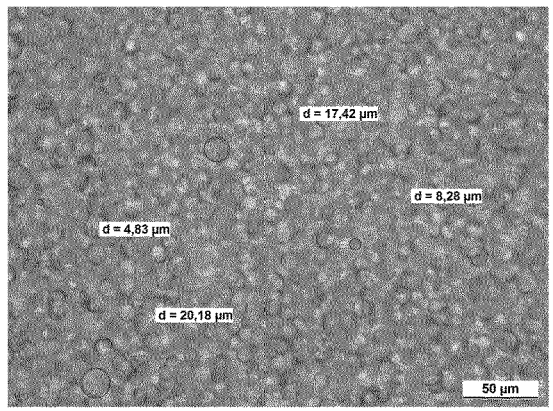
FIG. 6A depicts the buprenorphine-containing biphasic coating mixture of Comparative Example 3.
Figure 6B:
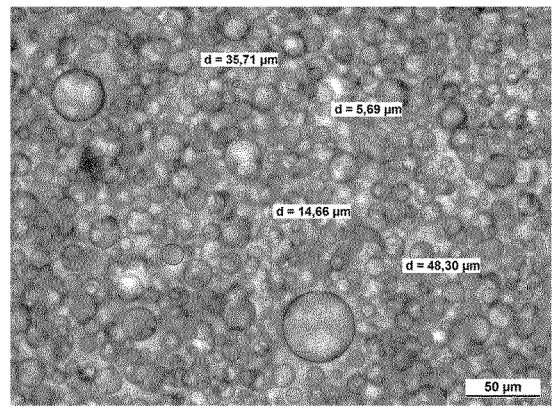
FIG. 6B depicts the buprenorphine-containing biphasic matrix layer of Comparative Example 3.

Microscopic pictures were taken of the buprenorphine base-containing adhesive mixture and of the matrix layer using a Nikon S/N 237789 Microscope. FIG. 6A shows a microscopic picture of the buprenorphine base-containing adhesive mixture of Comparative example 3 and FIG. 6B shows a microscopic picture of the matrix layer of Comparative example 3. During the microscopic investigation the droplet size (diameter) of the droplets in the matrix layer and the size of the spheres (diameter) in the matrix layer were determined. The maximum droplet sizes in the coating mixture and the maximum sphere size in the matrix layer are summarized in Table 13 below.

TABLE 13

| Comparative example 3 | |
| --- | --- |
| Maximum droplet size coating mixture (FIG. 6A) | Maximum sphere size matrix layer (FIG. 6B) |
| 20 μm | 48 μm |

Example 4

The composition of a buprenorphine base-containing adhesive coating mixture is summarized in Table 14 below.

TABLE 14

| Ingredient (Trade Name) | Amt/unit (g) |
| --- | --- |
| Buprenorphine base | 12.8 |
| Levulinic acid | 8.96 |
| Ethanol | 12.8 |
| PEG-12 Dimethicon (DC 5329 from Dow Corning Healthcare) | 3.2 |
| Cyclopentasiloxan/PEG/PPG-19/19 Dimethicon (DC BY 11-030 from Dow Corning Healthcare) | 3.84 |
| Polysiloxane adhesive in n-heptane Solids content of 73% by weight (BIO-PSA 7-4201 from Dow Corning Healthcare) | 135.9 |
| n-heptane | 3.0 |
| Total | 180.5 |

In a suitable vessel, e.g. a stainless steel or glass vessel, 12.8 g of buprenorphine was suspended in 8.96 g of levulinic acid, 12.8 g ethanol, 3.2 g PEG-12 Dimethicon and 3.84 g Cyclopentasiloxan/PEG/PPG-19/19 Dimethicon until complete dissolution of buprenorphine. 135.9 g of a polysiloxane adhesive in the form of a solution in n-heptane having a solids content of 73% by weight and 3.0 g of n-heptane to adjust the solids content were added. The mixture was stirred until homogeneous to give 180.5 g of a buprenorphine-containing adhesive mixture with 7.09% by weight of buprenorphine, with a solids content of 70.9%.

The buprenorphine-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 10% by weight of buprenorphine, 7% by weight of levulinic acid, 2.5% by weight of PEG-12 Dimethicon and 3% by weight of Cyclopentasiloxan/PEG/PPG-19/19 Dimethicon in this matrix layer.

The biphasic matrix layer was laminated with the backing layer to provide the buprenorphine-containing layer structure.

The individual systems (TTS) were then punched from the buprenorphine-containing layer structure.

In specific embodiments a TTS as described above can be provided with an adhesive overlay. The overlay is laminated onto the punched or cut individual systems which are then punched out by only punching the overlay and sealed into pouches of the primary packaging material.

Figure 7A:
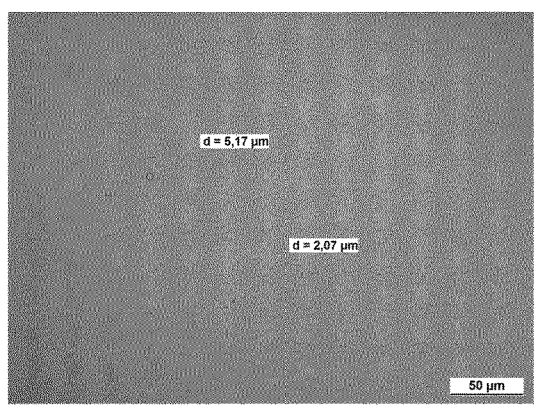
FIG. 7A depicts the buprenorphine-containing biphasic coating mixture of Example 4.
Figure 7B:
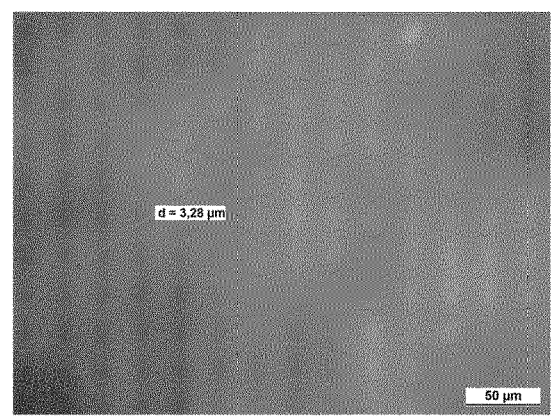
FIG. 7B depicts the buprenorphine-containing biphasic matrix layer of Example 4.

Microscopic pictures were taken of the buprenorphine base-containing adhesive coating mixture and the matrix layer using a Nikon S/N 237789 Microscope. FIG. 7A shows a microscopic picture of the buprenorphine-containing adhesive coating mixture of Example 4 and FIG. 7B shows a microscopic picture of the matrix layer of Example 4. During the microscopic investigation the droplet size (diameter) in the matrix layer and the size of the spheres (diameter) in the matrix layer were determined. FIG. 7B shows that in the dried matrix layer an enlargement of spheres has not taken place. The maximum droplet sizes in the coating mixture and the maximum sphere size in the matrix layer are summarized in Table 15 below.

TABLE 15

| Example 4 | |
| --- | --- |
| Maximum droplet size coating mixture (FIG. 7A) | Maximum sphere size matrix layer (FIG. 7B) |
| 5 μm | 3 μm |

Example 5

The composition of a buprenorphine base-containing adhesive coating mixture is summarized in Table 16 below.

TABLE 16

| Ingredient (Trade Name) | Amt/unit (g) |
| --- | --- |
| Buprenorphine base | 12.5 |
| Levulinic acid | 8.8 |
| Polyvinylpyrrolidone (PVP, K-Value 90) in Ethanol Solids content of 25% by weight | 12.5 |
| Ethanol | 8.3 |
| PEG-12 Dimethicon (DC 5329 from Dow Corning Healthcare) | 1.8 |
| Cyclopentasiloxan/PEG/PPG-19/19 Dimethicon (DC BY 11-030 from Dow Corning Healthcare) | 2.1 |
| Polysiloxane adhesive in n-heptane Solids content of 73% by weight (BIO-PSA 7-4201 from Dow Corning Healthcare) | 133.8 |
| n-heptane | 3.0 |
| Total | 182.8 |

In a suitable vessel, e.g. a stainless steel or glass vessel, 12.5 g of buprenorphine was suspended in 8.8 g of levulinic acid, 12.5 g of a PVP solution, 8.3 g ethanol, 1.8 g PEG-12 Dimethicon and 2.1 g Cyclopentasiloxan/PEG/PPG-19/19 Dimethicon and stirred until complete dissolution of buprenorphine. 133.8 g of a polysiloxane adhesive in the form of a solution in n-heptane having a solids content of 73% by weight and 3.0 g of n-heptane to adjust the solids content were added. The mixture was stirred until homogeneous to give 182.8 g of a buprenorphine-containing adhesive mixture with 6.84% by weight of buprenorphine, with a solids content of 68.4%.

The buprenorphine-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 10% by weight of buprenorphine, 7% by weight of levulinic acid, 2.5% by weight of Polyvinylpyrrolidone (PVP), 1.4% by weight of PEG-12

Dimethicon and 1.7% by weight of Cyclopentasiloxan/PEG/PPG-19/19 Dimethicon in this matrix layer.

The biphasic matrix layer was laminated with the backing layer to provide the buprenorphine-containing layer structure.

The individual systems (TTS) were then punched from the buprenorphine-containing layer structure.

In specific embodiments a TTS as described above can be provided with an adhesive overlay. The overlay is laminated onto the punched or cut individual systems and is then punched out by only punching the overlay and sealed into pouches of the primary packaging material.

Figure 8A:
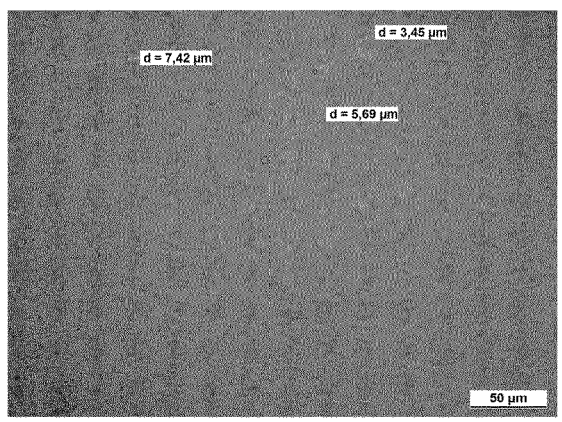
FIG. 8A depicts the buprenorphine-containing biphasic coating mixture of Example 5.
Figure 8B:
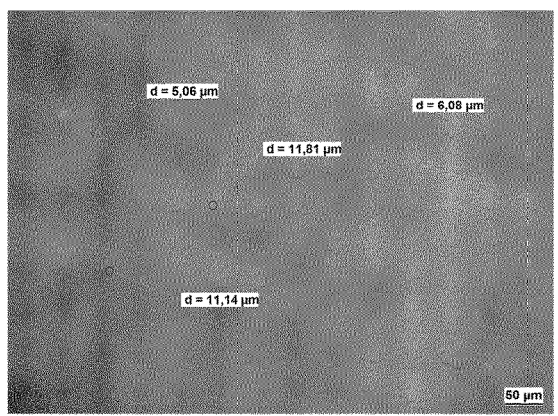
FIG. 8B depicts the buprenorphine-containing biphasic matrix layer of Example 5.

Microscopic pictures were taken of the buprenorphine base-containing adhesive coating mixture and the matrix layer using a Nikon S/N 237789 Microscope. FIG. 8A shows a microscopic picture of the buprenorphine-containing adhesive coating mixture of Example 5 and FIG. 8B shows a microscopic picture of the matrix layer of Example 5. During the microscopic investigation the droplet size in the matrix layer (diameter) and the size of the spheres (diameter) in the matrix layer were determined. FIG. 8B shows that in the dried matrix layer an enlargement of spheres has not taken place. The maximum droplet sizes in the coating mixture and the maximum sphere size in the matrix layer are summarized in Table 17 below.

TABLE 17

| Example 5 | |
|---|---|
| Maximum droplet size coating mixture (FIG. 8A) | Maximum sphere size matrix layer (FIG. 8B) |
| 7 μm | 12 μm |

Example 6

In Example 6, the in vitro skin permeations of Comparative example 3, Example 4, Example 5, and Norspan® were determined by in vitro experiments in accordance with the OECD Guideline (adopted Apr. 13, 2004) carried out with the Franz diffusion cell (a 9 ml Franz diffusion cell). Split thickness human skin from cosmetic surgeries (female abdomen, date of birth 1986 was used. A dermatome was used to prepare skin to a thickness of 800 μm, with an intact epidermis. Due to the prolonged test (168 hours) 800 μm skin is used instead of the recommended 200 to 400 μm skin.

Figure 9A:
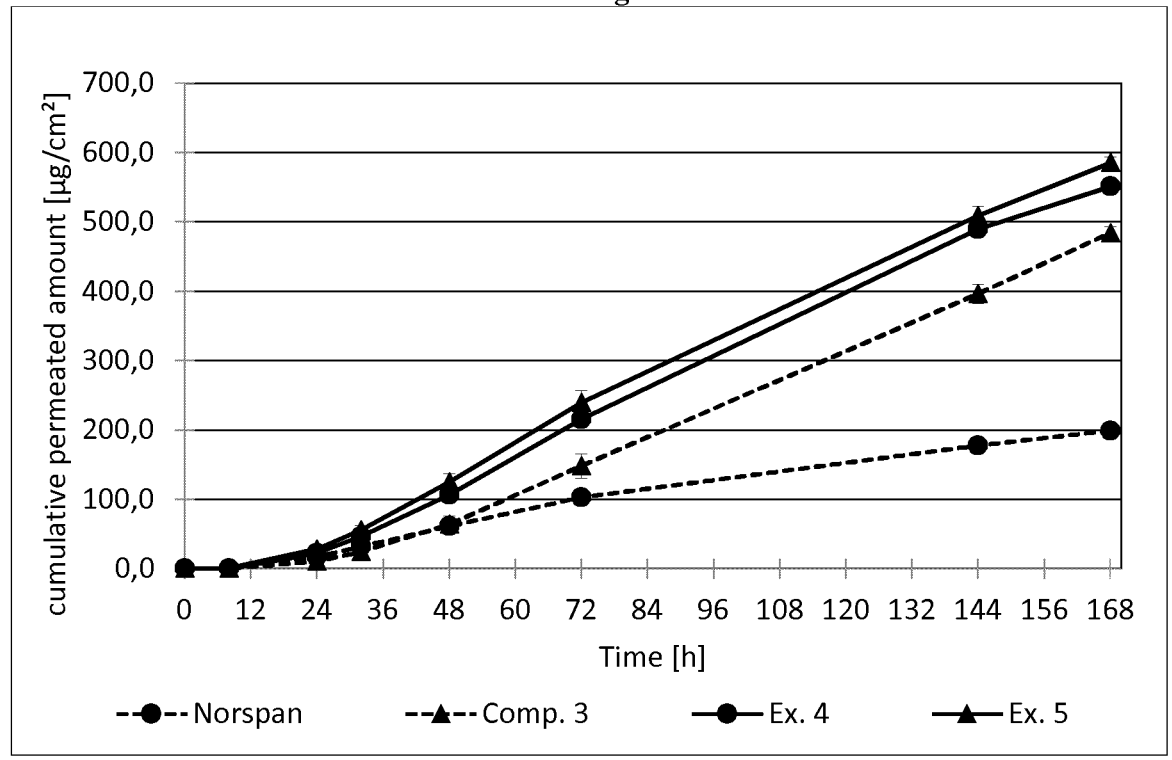
FIG. 9A depicts the cumulative permeated amount of Norspan®, Comparative Example 3, Example 4, and Example 5 over a time interval of 168 hours.
Figure 9B:
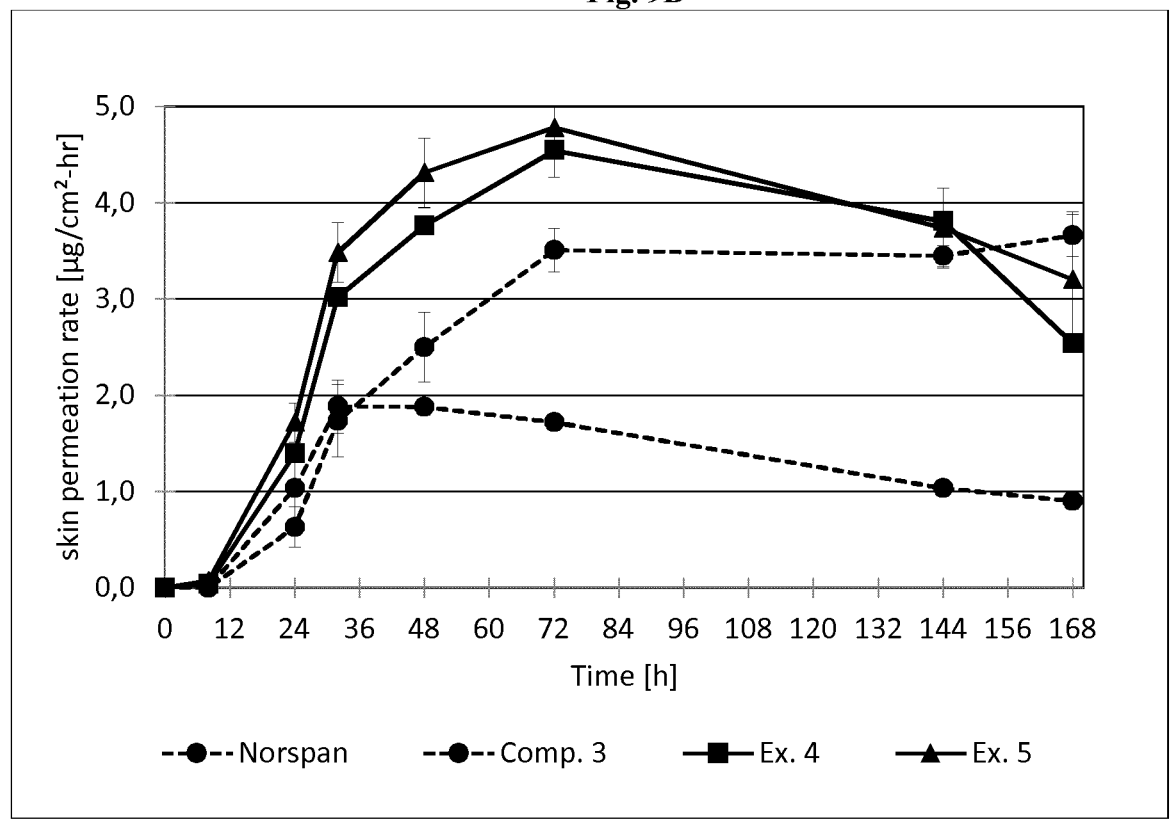
FIG. 9B depicts the skin permeation rate of Norspan®, Comparative Example 3, Example 4, and Example 5 over a time interval of 168 hours.

The receptor medium used is a phosphate buffer solution pH 5.5 with 0.1% saline azide as antibacteriological agent is used at a temperature of 32±1° C. Die cuts with an area of 1.191 cm² were punched from Comparative example 3, Example 4 and Example 5 and were tested against 1.191 cm² die cuts of the commercial product Norspan® Patch. The concentrations of buprenorphine in the receptor medium of the Franz cell at a temperature of 32±1° C. were measured. The results are shown in Tables 18 to 20 and FIGS. 9A and 9B.

TABLE 18

| cumulative permeated amount after certain elapsed time [μg/cm²] n = 3 (RSD in %) | | | | |
|---|---|---|---|---|
| Elapsed time (hr) | Comparative example 3 | Example 4 | Example 5 | Norspan® |
| 0 | 0 | 0 | 0 | 0 |
| 8 | — (—) | 0.891 (—) | 0.812 (32) | — (—) |
| 24 | 10.1 (33) | 22.6 (25) | 28.0 (12) | 16.5 (31) |
| 32 | 24.0 (27) | 46.7 (20) | 55.9 (9) | 31.6 (23) |
| 48 | 64.0 (19) | 107 (15) | 125 (7) | 61.6 (14) |
| 72 | 148 (12) | 216 (10) | 240 (8) | 103 (7) |
| 144 | 396 (4) | 490 (7) | 509 (10) | 177 (1) |
| 168 | 484 (2) | 551 (9) | 585 (11) | 199 (1) |

TABLE 19

| permeated amount [μg/cm²] n = 3 (RSD in %) | | | | |
|---|---|---|---|---|
| Elapsed time (hr) | Comparative example 3 | Example 4 | Example 5 | Norspan® |
| 0 | 0 | 0 | 0 | 0 |
| 8 | — (—) | 0.297 (—) | 0.812 (32) | — (—) |
| 24 | 10.1 (33) | 22.3 (23) | 27.5 (12) | 16.5 (31) |
| 32 | 13.9 (22) | 24.1 (17) | 27.9 (9) | 15.1 (15) |
| 48 | 40.0 (14) | 60.2 (12) | 69.0 (8) | 30.0 (4) |
| 72 | 84.2 (7) | 109 (7) | 115 (11) | 41.3 (3) |
| 144 | 248 (3) | 274 (11) | 269 (11) | 74.4 (8) |
| 168 | 87.8 (6) | 60.9 (31) | 76.8 (22) | 21.6 (10) |

TABLE 20

| skin permeation rate [μg/cm² × hr] n = 3 (SD) | | | | |
|---|---|---|---|---|
| Elapsed time (hr) | Comparative example 3 | Example 4 | Example 5 | Norspan® |
| 0 | 0 | 0 | 0 | 0 |
| 8 | — (—) | 0.04 (0.06) | 0.07 (0.06) | — (—) |
| 24 | 0.63 (0.21) | 1.39 (0.32) | 1.72 (0.20) | 1.03 (0.32) |
| 32 | 1.73 (0.38) | 3.02 (0.52) | 3.48 (0.31) | 1.88 (0.28) |
| 48 | 2.50 (0.36) | 3.76 (0.44) | 4.31 (0.36) | 1.88 (0.08) |
| 72 | 3.51 (0.23) | 4.54 (0.31) | 4.78 (0.51) | 1.72 (0.05) |
| 144 | 3.44 (0.11) | 3.81 (0.43) | 3.74 (0.42) | 1.03 (0.08) |
| 168 | 3.66 (0.22) | 2.54 (0.78) | 3.20 (0.71) | 0.90 (0.09) |

Example 7

The composition of a buprenorphine base-containing adhesive coating mixture is summarized in Table 21 below.

TABLE 21

| Ingredient (Trade Name) | Amt/unit (g) |
| --- | --- |
| Buprenorphine base | 4.5 |
| Levulinic acid | 5.1 |
| Ethanol | 4.5 |
| PEG-12 Dimethicon (DC 5329 from Dow Corning Healthcare) | 2.8 |
| Cyclopentasiloxan/PEG/PPG-19/19 Dimethicon (DC BY 11-030 from Dow Corning Healthcare) | 4.0 |
| Polysiloxane adhesive in n-heptane Solids content of 72.3% by weight (BIO-PSA 7-4201 from Dow Corning Healthcare) | 79.1 |
| Total | 100.0 |

In a suitable vessel, e.g. a stainless steel or glass vessel, 4.5 g of buprenorphine was suspended in 5.1 g of levulinic acid, 4.5 g ethanol, 2.8 g PEG-12 Dimethicon and 4 g Cyclopentasiloxan/PEG/PPG-19/19 Dimethicon until complete dissolution of buprenorphine. 79.1 g of a polysiloxane adhesive in the form of a solution in n-heptane having a solids content of 72.3% by weight were added. The mixture was stirred until homogeneous to give 100 g of a buprenorphine-containing adhesive mixture with 4.5% by weight of buprenorphine, with a solids content of 73.6%.

The buprenorphine-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 6.1% by weight of buprenorphine, 6.9% by weight of levulinic acid, 3.8% by weight of PEG-12 Dimethicon and 5.4% by weight of Cyclopentasiloxan/PEG/PPG-19/19 Dimethicon in this matrix layer.

The biphasic matrix layer was laminated with the backing layer to provide the buprenorphine-containing layer structure.

The individual systems (TTS) were then punched from the buprenorphine-containing layer structure.

In specific embodiments a TTS as described above can be provided with an adhesive overlay. The overlay is laminated onto the punched or cut individual systems which are then punched out by only punching the overlay and sealed into pouches of the primary packaging material.

Figure 10A:
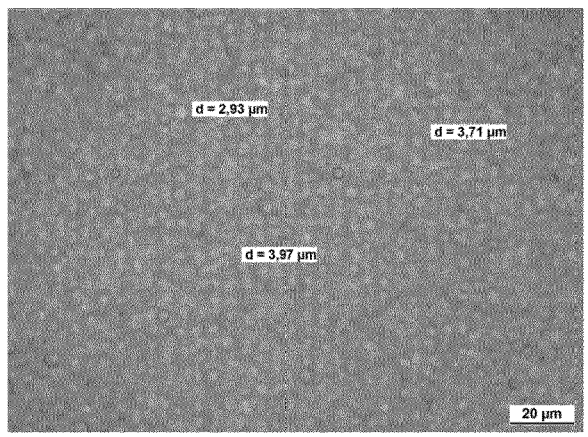
FIG. 10A depicts the buprenorphine-containing biphasic coating mixture of Example 7.
Figure 10B:
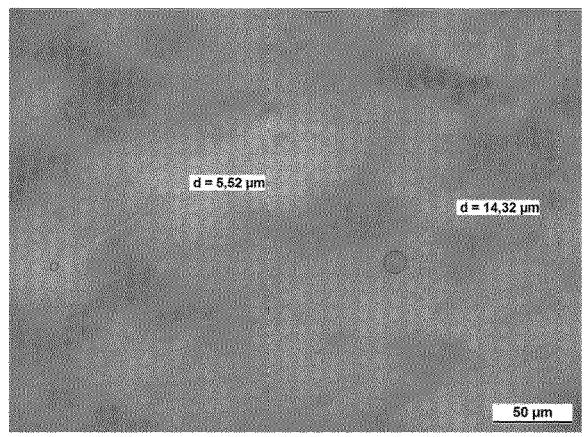
FIG. 10B depicts the buprenorphine-containing biphasic matrix layer of Example 7.

Microscopic pictures were taken of the buprenorphine base-containing adhesive coating mixture and the matrix layer using a Nikon S/N 237789 Microscope. FIG. 10A shows a microscopic picture of the buprenorphine-containing adhesive coating mixture of Example 7 and FIG. 10B shows a microscopic picture of the matrix layer of Example 7. During the microscopic investigation the droplet size in the matrix layer (diameter) and the size of the spheres (diameter) in the matrix layer were determined. FIG. 10B shows that in the dried matrix layer an enlargement of spheres has not taken place. The maximum droplet sizes in the coating mixture and the maximum sphere size in the matrix layer are summarized in Table 22 below.

TABLE 22

| Example 7 | |
| --- | --- |
| Maximum droplet size coating mixture (FIG. 10A) | Maximum sphere size matrix layer (FIG. 10B) |
| 4 μm | 14 μm |

Example 8

The composition of a buprenorphine base-containing adhesive coating mixture is summarized in Table 23 below.

TABLE 23

| Ingredient (Trade Name) | Amt/unit (g) |
| --- | --- |
| Buprenorphine base | 4.5 |
| Levulinic acid | 5.1 |
| Ethanol | 4.5 |
| PEG-12 Dimethicon (DC 5329 from Dow Corning Healthcare) | 2.0 |
| Cyclopentasiloxan/PEG/PPG-19/19 Dimethicon (DC BY 11-030 from Dow Corning Healthcare) | 3.0 |
| Polysiloxane adhesive in n-heptane Solids content of 73% by weight (BIO-PSA 7-4201 from Dow Corning Healthcare) | 80.9 |
| Total | 100.0 |

In a suitable vessel, e.g. a stainless steel or glass vessel, 4.5 g of buprenorphine was suspended in 5.1 g of levulinic acid, 4.5 g ethanol, 2.0 g PEG-12 Dimethicon and 3.0 g Cyclopentasiloxan/PEG/PPG-19/19 Dimethicon until complete dissolution of buprenorphine. 80.9 g of a polysiloxane adhesive in the form of a solution in n-heptane having a solids content of 72.3% by weight were added. The mixture was stirred until homogeneous to give 100 g of a buprenorphine-containing adhesive mixture with 4.5% by weight of buprenorphine, with a solids content of 73.1%.

The buprenorphine-containing adhesive mixture was coated on an abhesively equipped foil using a laboratory roll coater in order to mimic the coating process in pilot and commercial plants and to apply representative shear forces.

The coating thickness was chosen such that removal of the solvents results in an area weight of the matrix layer of approx. 90 g/m$^2$. This results in 6.2% by weight of buprenorphine, 7.0% by weight of levulinic acid, 2.7% by weight of PEG-12 Dimethicon and 4.1% by weight of Cyclopentasiloxan/PEG/PPG-19/19 Dimethicon in this matrix layer.

The biphasic matrix layer was laminated with the backing layer to provide the buprenorphine-containing layer structure.

The individual systems (TTS) were then punched from the buprenorphine-containing layer structure.

In specific embodiments a TTS as described above can be provided with an adhesive overlay. The overlay is laminated onto the punched or cut individual systems and is then punched out by only punching the overlay and sealed into pouches of the primary packaging material.

Figure 11A:
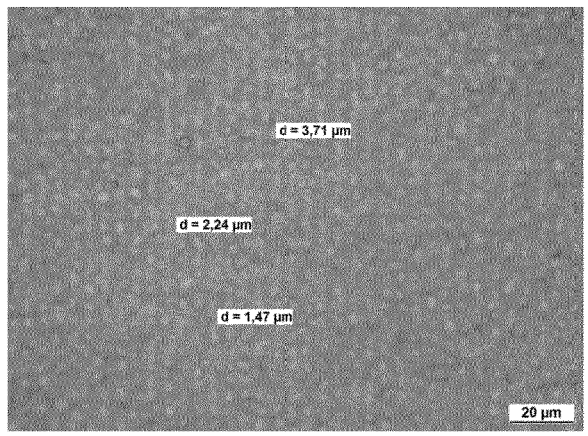
FIG. 11A depicts the buprenorphine-containing biphasic coating mixture of Example 8.
Figure 11B:
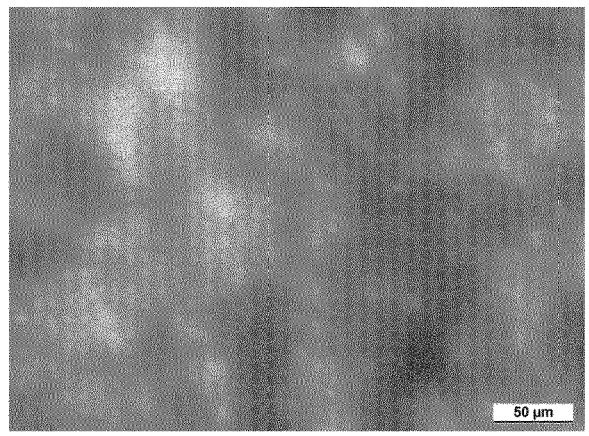
FIG. 11B depicts the buprenorphine-containing biphasic matrix layer of Example 8.

Microscopic pictures were taken of the buprenorphine base-containing adhesive coating mixture and the matrix layer using a Nikon S/N 237789 Microscope. FIG. 11A shows a microscopic picture of the buprenorphine-containing adhesive coating mixture of Example 8 and FIG. 11B shows a microscopic picture of the matrix layer of Example 8. During the microscopic investigation the droplet size (diameter) in the coating mixture and the size of the spheres in the matrix layer (diameter) were determined. The maximum size of the spheres in the matrix layer was smaller than 1 μm and was therefore not depicted in FIG. 11B. The maximum droplet sizes in the coating mixture and the maximum sphere size in the matrix layer are summarized in Table 24 below.

TABLE 24

Example 8

| Maximum droplet size coating mixture (FIG. 11A) | Maximum sphere size matrix layer (FIG. 11B) |
|---|---|
| 4 μm | <1 μm |

Example 9

Figure 12A:
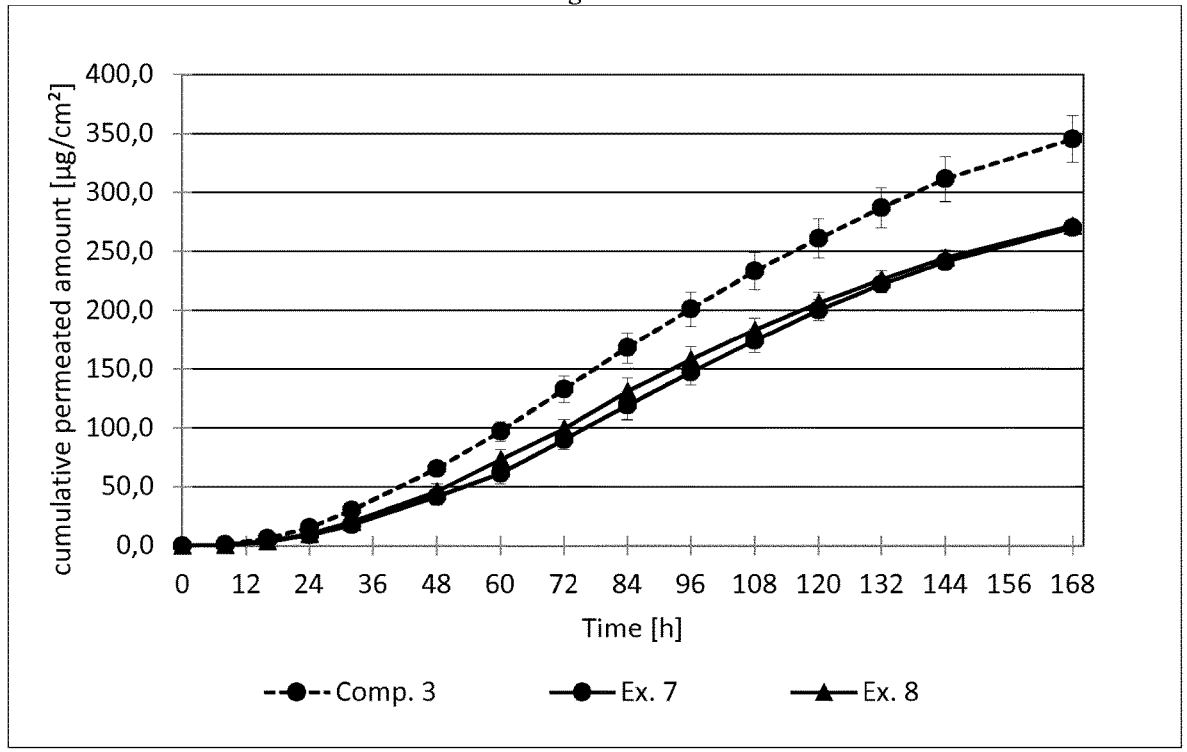
FIG. 12A depicts the cumulative permeated amount of Comparative Example 3, Example 7, and Example 8 over a time interval of 168 hours.
Figure 12B:
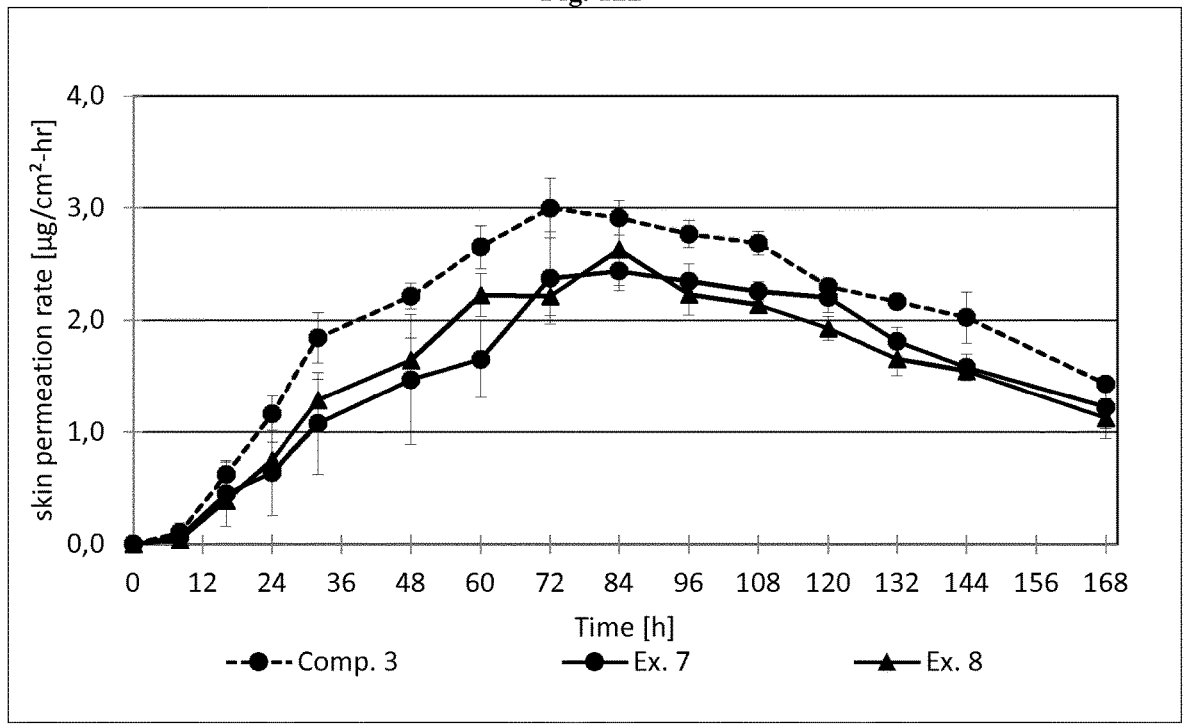
FIG. 12B depicts the skin permeation rate of Comparative Example 3, Example 7, and Example 8 over a time interval of 168 hours.

In Example 9, the in vitro skin permeations of Comparative example 3 and Example 7 and 8 were determined by in vitro experiments carried out with the Microette Plus™-system by Hanson Research Corp. (Chatsworth CA, USA), which provides automatic sampling from diffusion cells and collecting into HPLC-vials for sample analysis. The Microette Plus™-system works with vertical diffusion cells, first popularized by Dr. Thomas Franz (J. of Invest. Dermatology, 64:190-195, 1975). As diffusion cells a 7 ml receptor medium was used. Split thickness human skin from cosmetic surgeries (male abdomen, date of birth 1974) was used. A dermatome was used to prepare skin to a thickness of 800 with an intact epidermis. Due to the prolonged test (168 hours) 800 μm skin is used instead of the recommended 200 to 400 μm skin. The receptor medium used is a phosphate buffer solution pH 5.5 with 0.1% saline azide as antibacteriological agent is used at a temperature of 32±1° C. Die cuts with an area of 1.16 cm² were punched from Example 7 and 8 and were tested against Comparative example 3 using 1.16 cm² die cuts. At the sampling intervals the medium is automatically partially (aliquots of 2.5 ml) removed and replaced by an equivalent volume of fresh medium. The concentrations of buprenorphine in the receptor medium of the cell at a temperature of 32±1° C. were measured by HPLC analysis. The results are shown in Tables 25 to 27 and FIGS. 12A and 12B.

TABLE 25 cumulative permeated amount after certain elapsed time [μgg/cm²] n = 3 (RSD in %)

| Elapsed time (hr) | Comparative example 3 | Example 7 | Example 8 |
|---|---|---|---|
| 0 | 0 | 0 | 0 |
| 8 | 0.855 (77) | 0.501 (131) | 0.328 (48) |
| 16 | 5.80 (18) | 4.07 (73) | 3.44 (21) |
| 24 | 15.06 (16) | 9.16 (66) | 9.41 (21) |
| 32 | 29.8 (14) | 17.8 (54) | 19.7 (18) |
| 48 | 65.2 (9) | 41.2 (45) | 46.0 (14) |
| 60 | 97.0 (8) | 61.1 (34) | 72.7 (12) |
| 72 | 133 (8) | 89.6 (28) | 99.2 (8) |
| 84 | 168 (8) | 119 (19) | 131 (9) |
| 96 | 201 (7) | 147 (20) | 158 (7) |
| 108 | 233 (7) | 174 (17) | 183 (6) |
| 120 | 261 (6) | 200 (14) | 206 (4) |
| 132 | 287 (6) | 222 (12) | 226 (3) |
| 144 | 311 (6) | 241 (10) | 245 (3) |
| 168 | 346 (6) | 270 (9) | 272 (1) |

TABLE 26 permeated amount [μg/cm²] n = 3 (RSD in %)

| Elapsed time (hr) | Comparative example 3 | Example 7 | Example 8 |
|---|---|---|---|
| 0 | 0 | 0 | 0 |
| 8 | 0.855 (77) | 0.501 (131) | 0.328 (48) |
| 16 | 4.94 (21) | 3.57 (65) | 3.11 (18) |
| 24 | 9.3 (14) | 5.10 (60) | 5.97 (21) |
| 32 | 14.7 (12) | 8.62 (42) | 10.3 (15) |
| 48 | 35.4 (5) | 23.5 (42) | 26.3 (12) |
| 60 | 31.8 (7) | 19.8 (21) | 26.7 (9) |
| 72 | 35.9 (9) | 28.5 (17) | 26.6 (8) |
| 84 | 34.9 (5) | 29.2 (7) | 31.6 (12) |
| 96 | 33.2 (4) | 28.2 (7) | 26.8 (8) |
| 108 | 32.3 (4) | 27.0 (4) | 25.7 (3) |
| 120 | 27.6 (3) | 26.4 (6) | 23.1 (6) |
| 132 | 26.0 (3) | 21.7 (7) | 19.9 (9) |
| 144 | 24.3 (11) | 19.0 (7) | 18.6 (5) |
| 168 | 34.3 (2) | 29.3 (16) | 27.0 (16) |

TABLE 27 skin permeation rate [μg/cm² × hr] n = 3 (SD)

| Elapsed time (hr) | Comparative example 3 | Example 7 | Example 8 |
|---|---|---|---|
| 0 | 0 | 0 | 0 |
| 8 | 0.11 (0.08) | 0.06 (0.08) | 0.04 (0.02) |
| 16 | 0.62 (0.13) | 0.45 (0.29) | 0.39 (0.07) |
| 24 | 1.16 (0.16) | 0.64 (0.38) | 0.75 (0.16) |
| 32 | 1.84 (0.23) | 1.08 (0.46) | 1.28 (0.19) |
| 48 | 2.21 (0.12) | 1.47 (0.58) | 1.65 (0.20) |
| 60 | 2.65 (0.19) | 1.65 (0.34) | 2.23 (0.19) |
| 72 | 3.00 (0.26) | 2.38 (0.41) | 2.21 (0.17) |
| 84 | 2.91 (0.15) | 2.44 (0.17) | 2.63 (0.32) |
| 96 | 2.77 (0.12) | 2.35 (0.15) | 2.23 (0.19) |
| 108 | 2.69 (0.10) | 2.25 (0.09) | 2.14 (0.06) |
| 120 | 2.30 (0.07) | 2.20 (0.13) | 1.93 (0.11) |
| 132 | 2.16 (0.06) | 1.81 (0.13) | 1.66 (0.15) |
| 144 | 2.02 (0.23) | 1.58 (0.12) | 1.55 (0.08) |
| 168 | 1.43 (0.03) | 1.22 (0.19) | 1.12 (0.18) |

Example 10

Figure 13A:
FIG. 13A depicts the results of the blending test according to Examples 10a to 10 h.
Figure 13A:
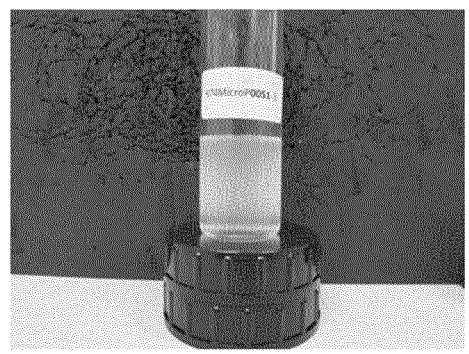
Figure 13A:
Figure 13A:
Figure 13A:
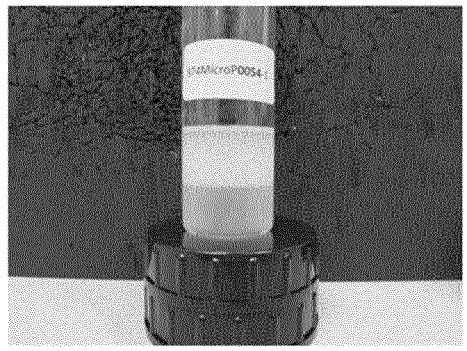
Figure 13A:
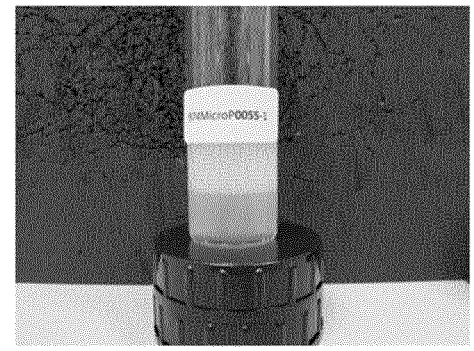
Figure 13A:
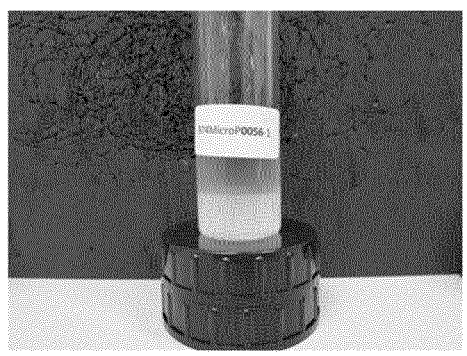
Figure 13A:
Figure 13B:
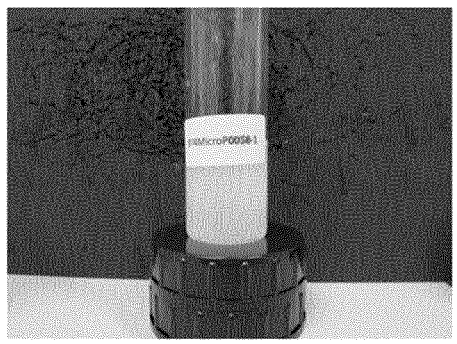
FIG. 13B depicts the results of the blending test according to Examples 10i to 10r.
Figure 13B:
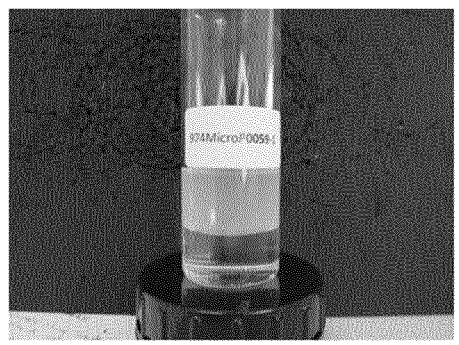
Figure 13B:
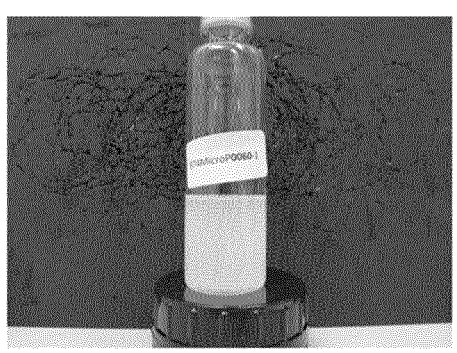
Figure 13B:
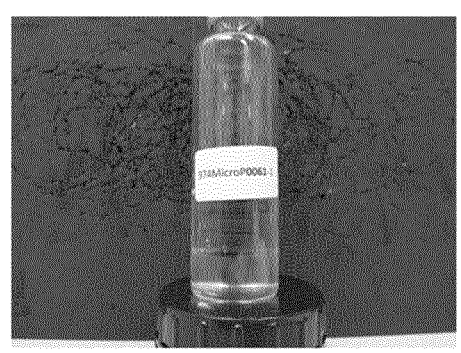
Figure 13B:
Figure 13B:
Figure 13B:
Figure 13B:
Figure 13B:
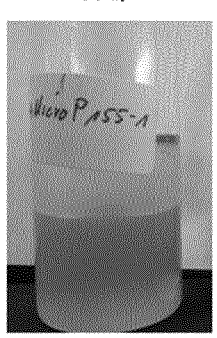
Figure 13B:
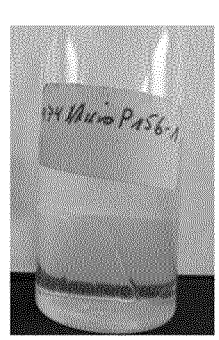

In Example 10, suitable emulsifier for the outer phase of a biphasic system were determined by mixing 10 g of an adhesive (e.g. Dow Corning® BIO-PSA 7-4201) and 10 g of a potential emulsifier in a transparent 50 ml test tube. The test tubes were sealed and shaked for about 1 hour on a mechanical shaker (using an IKA Vibrax-VXR adjusted between the configurations 3 to 5 from 10). After expiry of the shaking time the test tubes were stored at room temperature within the lab (about 20° C.) for about 24 hours. Subsequently, pictures were taken of the test tubes, and the contained mixtures were examined for phase separation. The proportion of a separated phase in the mixture can be determined by comparing the height of the separated phase in the test tube in cm and the height of the total content in the test tube in cm (e.g., measured with a ruler from the bottom of the test tube to the lowest point of the meniscus of the phase). For example, if the height of the separated phase in the test tube is 1 cm and the total content in the test tube is 4 cm in height, the phase separation is 25%. Complete phase separation occurs when each phase amounts to 50% of the total content. If the separated phase amounted to less than 20% of the total content in the test tube, the emulsifier was considered suitable for the tested adhesive. The results of this pre-test are shown in Tables 28 and FIGS. 13A and 13B.

TABLE 28

| Sample | Adhesive | Emulsifier | Evaluation |
|---|---|---|---|
| A | Polysiloxane adhesive dissolved in n-Heptane (Dow Corning ® BIO-PSA 7-4201) | Cyclopentasiloxane (and) PEG-12 Dimethicone Crosspolymer (Dow Corning ® 9011 Silicone Elastomer Blend) | Suitable emulsifier (no phase separation or phase separation <20%, picture 13A) |
| B | | Cyclopentasiloxane (and) PEG/PPG-19/19 Dimethicone (Dow Corning ® BY 11-030) | Suitable emulsifier (no phase separation or phase separation <20%, picture 13B) |
| C | | Cyclopentasiloxane (and) PEG/PPG-18/18 Dimethicone (Dow Corning ® 5225C Formulation Aid) | Suitable emulsifier (no phase separation or phase separation <20%, picture 13C) |
| D | | PEG-12 Dimethicone (Dow Corning ® 5329) | Suitable emulsifier (no phase separation or phase separation <20%, picture 13D) |
| E | | Polyoxyethylen(20)-sorbitan-monolaurat (Tween ® 20) | Phase separation >20%, picture 13E |
| F | | Polyoxyethylen(20)-sorbitan-monooleat (Tween ® 80) | Phase separation >20%, picture 13F |
| G | | Polyoxyethylen(20)-sorbitan-trioleat (Tween ® 85) | Phase separation >20%, picture 13G |
| H | | Sorbitanmonooleat (Span 80) | Phase separation >20%, picture 13 H |
| I | | Polyoxyl 35 Hydrogenated Castor oil (Cremophor ® ELP) | Suitable emulsifier (no phase separation or phase separation <20%, picture 13I) |
| J | | Caprylocaproyl polyoxylglycerides (Labrasol ®) | Phase separation >20%, picture 13J |
| K | | Polyoxypropylene-Polyoxyethylene Block Copolymer (Lutrol ® L44) | Suitable emulsifier (no phase separation or phase separation <20%, picture 13K) |
| L | | Polyoxyethylen (4) laurylether (Brij ® 30) | Phase separation >20%, picture 13L |
| M | | Polyoxyethylene (10) oleyl ether (Brij ® 97) | Phase separation >20%, picture 13K |
| N | | Glyceryl Oleate (Imwitor ® 948) | Phase separation >20%, picture 13N |
| O | Polyisobutylene/Polybutylene adhesive dissolved in Hexane (PIB B10/B100 (85%/15%) from BASF SE) | Cyclopentasiloxane (and) PEG-12 Dimethicone Crosspolymer (Dow Corning ® 9011 Silicone Elastomer Blend) | Suitable emulsifier (no phase separation or phase separation <20%, picture 13O) |
| P | | Cyclopentasiloxane (and) PEG/PPG-18/18 Dimethicone (Dow Corning ® 5225C Formulation Aid) | Suitable emulsifier (no phase separation or phase separation <20%, picture 13P) |
| Q | | Sorbitanmonooleat (Span ® 80) | Phase separation >20%, picture 13Q |
| R | | Glyceryl Oleate (Imwitor ® 948) | Phase separation >20%, picture 13R |

The Invention Relates in Particular to the Following Further Items

1. Transdermal therapeutic system for the transdermal administration of an active agent comprising an active agent-containing layer structure, the active agent-containing layer structure comprising A) a backing layer, and B) a biphasic matrix layer, the biphasic matrix layer having a) a continuous, outer phase having a composition comprising 70 to 100% by weight of at least one polymer, b) a discontinuous, inner phase having a composition comprising the active agent and a dissolver for the active agent in amount sufficient so that the active agent forms a solution with the dissolver in the inner phase, wherein the discontinuous, inner phase forms dispersed deposits in the continuous, outer phase, and c) an emulsifier in an amount of 0.1 to 20% by weight based on the biphasic matrix layer, wherein the emulsifier is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.

2. Transdermal therapeutic system in accordance with item 1, wherein the biphasic matrix layer contains 0.1 to less than 20% by weight of the emulsifier.

3. Transdermal therapeutic system in accordance with item 1, wherein the biphasic matrix layer contains 0.5 to 10% by weight of the emulsifier.

4. Transdermal therapeutic system in accordance with item 1, wherein the biphasic matrix layer contains 0.5 to 8% by weight of the emulsifier.

5. Transdermal therapeutic system in accordance with item 1, wherein the biphasic matrix layer contains 0.5 to 5% by weight of the emulsifier.

6. Transdermal therapeutic system in accordance with any one of items 1 to 5, wherein the emulsifier is selected from the group consisting of an emulsifier based on polysiloxane, an emulsifier based on polyisobutylene, an emulsifier based on ethoxylated castor oil, an emulsifier based on poloxamer, and mixtures thereof.

7. Transdermal therapeutic system in accordance with any one of items 1 to 6, wherein the emulsifier is based on polysiloxane.

8. Transdermal therapeutic system in accordance with any one of items 1 to 7, wherein the emulsifier comprises at least one polydimethylsiloxane copolymerized or crosspolymerized with at least polyethylene glycol.

9. Transdermal therapeutic system in accordance with item 8, wherein the polyethylene glycol has an average number of ethylene oxide repeating units of 10 to 20.

10. Transdermal therapeutic system in accordance with item 8 or 9, wherein the at least one polydimethylsiloxane is copolymerized with polyethylene glycol and polypropylene glycol.

11. Transdermal therapeutic system in accordance with any one of item 10, wherein the polypropylene glycol has an average number of propylene oxide repeating units of 7 to 20.

12. Transdermal therapeutic system in accordance with any one of items 1 to 9, wherein the emulsifier is based on polysiloxanes selected from the group consisting of PEG-12 dimethicone crosspolymer, PEG-10 dimethicone, PEG-12 dimethicone, PEG/PPG-18/18 dimethicone, PEG/PPG-19/19 dimethicone, bis-isobutyl PEG/PPG-18/18 dimethicone copolymer, and mixtures thereof.

13. Transdermal therapeutic system in accordance with any one of items 1 to 9, wherein the emulsifier is based on polysiloxanes selected from the group consisting of PEG-12 dimethicone crosspolymer, PEG-12 dimethicone, PEG/PPG-18/18 dimethicone, PEG/PPG-19/19 dimethicone, and mixtures thereof.

14. Transdermal therapeutic system in accordance with any one of items 1 to 13, wherein the emulsifier is based on a mixture of PEG-12 dimethicone and PEG/PPG-19/19 dimethicone.

15. Transdermal therapeutic system in accordance with item 13, wherein the emulsifier is PEG-12 dimethicone.

16. Transdermal therapeutic system in accordance with any one of items 1 to 15, wherein the emulsifier is based on polysiloxane and is used as a dispersion, containing 1 to 95% by weight of a solvent.

17. Transdermal therapeutic system in accordance with any one of items 1 to 16, wherein the emulsifier is based on polysiloxane and is used as a dispersion, comprising a solvent selected from the group consisting of cyclopentasiloxane, dimethicone, and a mixture of C13-16 isoparaffin and C10-13 isoparaffin.

18. Transdermal therapeutic system in accordance with any one of items 1 to 9, wherein the emulsifier is based on PEG-12 dimethicone crosspolymer and is used as a dispersion, containing 85 to 90% by weight of cyclopentasiloxane.

19. Transdermal therapeutic system in accordance with any one of items 1 to 13, wherein the emulsifier is based on PEG/PPG-18/18 dimethicone and is used as a dispersion, containing 85 to 90% by weight of cyclopentasiloxane.

20. Transdermal therapeutic system in accordance with any one of items 1 to 13, wherein the emulsifier is based on PEG/PPG-19/19 dimethicone and is used as dispersion, containing 40 to 60% by weight of cyclopentasiloxane.

21. Transdermal therapeutic system in accordance with any one of items 1 to 13, wherein the emulsifier is based on a mixture of PEG-12 dimethicone and PEG/PPG-19/19 dimethicone and wherein PEG/PPG-19/19 dimethicone is used as a dispersion, containing 40 to 60% by weight of cyclopentasiloxane.

22. Transdermal therapeutic system in accordance with item 21, wherein the weight ratio of the PEG-12 dimethicone and the PEG/PPG-19/19 dimethicone dispersion is 0.5:1 to 1:5.

23. Transdermal therapeutic system in accordance with item 21, wherein the weight ratio of the PEG-12 dimethicone and the PEG/PPG-19/19 dimethicone dispersion is 1:1 to 1:3.

24. Transdermal therapeutic system in accordance with item 21, wherein the weight ratio of the PEG-12 dimethicone and the PEG/PPG-19/19 dimethicone dispersion is 1:1.1 to 1:2.3.

25. Transdermal therapeutic system in accordance with any one of items 1 to 6, wherein the emulsifier is based on polyisobutylene.

26. Transdermal therapeutic system in accordance with any one of items 1 to 6, and 25, wherein the emulsifier is a hydrophilic emulsifier based on polyisobutylene.

27. Transdermal therapeutic system in accordance with any one of items 1 to 6, 25, and 26, wherein the emulsifier comprises at least one polyisobutylene linked to a succinic acid derivative.

28. Transdermal therapeutic system in accordance with item 27, wherein the at least one polyisobutylene has a number average molecular weight of Mn=300 to 10,000.

29. Transdermal therapeutic system in accordance with any one of items 27 or 28, wherein the succinic acid derivative is linked to a hydrophilic compound comprising at least two polyethylene glycols having an average number of ethylene oxide repeating units of 1 to 50, or of 1 to 10.

30. Transdermal therapeutic system in accordance with any one of items 1 to 6, wherein the emulsifier is based on ethoxylated castor oil.

31. Transdermal therapeutic system in accordance with item 30, wherein the ethoxylated castor oil is selected from the group consisting of polyoxyl 35 hydrogenated castor oil, polyoxyl 40 castor oil, polyoxyl 40 hydrogenated castor oil, polyoxyl 60 hydrogenated castor oil, and mixtures thereof.
32. Transdermal therapeutic system in accordance with any one of items 1 to 6, wherein the emulsifier is polyoxyl 35 hydrogenated castor oil.
33. Transdermal therapeutic system in accordance with any one of items 1 to 6, wherein the emulsifier is based on poloxamer.
34. Transdermal therapeutic system in accordance with item 33, wherein the poloxamer is liquid at 20° C.
35. Transdermal therapeutic system in accordance with any one of items 33 or 34, wherein the two polyethylene oxide blocks of the poloxamer have an ethylene oxide repeating units number of 12 and the propylene oxide block of the poloxamer has a propylene oxide repeating units number of 20.
36. Transdermal therapeutic system in accordance with any one of items 1 to 35, wherein the at least one polymer in the continuous, outer phase is a hydrophobic polymer.
37. Transdermal therapeutic system in accordance with any one of items 1 to 36, wherein the at least one polymer in the continuous, outer phase is polysiloxane or polyisobutylene.
38. Transdermal therapeutic system in accordance with any one of items 1 to 37, wherein the composition of the continuous, outer phase is a pressure-sensitive adhesive composition.
39. Transdermal therapeutic system in accordance with any one of items 1 to 38, wherein the at least one polymer in the continuous, outer phase is a pressure-sensitive adhesive polymer.
40. Transdermal therapeutic system in accordance with any one of items 1 to 39, wherein the at least one polymer in the continuous, outer phase is a pressure-sensitive adhesive polymer based on polysiloxane or polyisobutylene.
41. Transdermal therapeutic system in accordance with any one of items 1 to 40, wherein the content of the discontinuous, inner phase in the biphasic matrix layer is from 5 to 40% by volume based on the volume of the biphasic matrix layer.
42. Transdermal therapeutic system in accordance with any one of items 1 to 41, wherein the dispersed deposits have a maximum sphere size of less than 20 µm.
43. Transdermal therapeutic system in accordance with any one of items 1 to 42, wherein the active agent is contained in the transdermal therapeutic system in an amount of from 1 to 50 mg.
44. Transdermal therapeutic system in accordance with any one of items 1 to 43, wherein the active agent is contained in an amount of from 1 to 30% by weight based on the biphasic matrix layer.
45. Transdermal therapeutic system in accordance with any one of items 1 to 44, wherein the active agent is contained in an amount of from 1 to 15% by weight based on the biphasic matrix layer.
46. Transdermal therapeutic system in accordance with any one of items 1 to 45, wherein the active agent is contained in an amount of from 2 to 12% by weight based on the biphasic matrix layer.
47. Transdermal therapeutic system in accordance with any one of items 1 to 46, wherein the active agent is contained in an amount of from 0.1 to 5 $mg/cm^2$ based on the biphasic matrix layer.
48. Transdermal therapeutic system in accordance with any one of items 1 to 48, wherein the active agent is contained in an amount of from 0.5 to 1.5 $mg/cm^2$ based on the biphasic matrix layer.
49. Transdermal therapeutic system in accordance with any one of items 1 to 48, wherein the active agent is contained in an amount of from 3 to 5 $mg/cm^2$ based on the biphasic matrix layer.
50. Transdermal therapeutic system in accordance with any one of items 1 to 49, wherein the active agent is selected from the group consisting of buprenorphine and diclofenac.
51. Transdermal therapeutic system in accordance with any one of items 1 to 50, wherein the active agent is buprenorphine base.
52. Transdermal therapeutic system in accordance with item 51, wherein the buprenorphine-containing layer is obtainable by incorporating the buprenorphine in the form of the free base.
53. Transdermal therapeutic system in accordance with any one of items 51 or 52, wherein buprenorphine base is contained in an amount of from 1 to 15% by weight of the biphasic matrix layer.
54. Transdermal therapeutic system in accordance with any one of items 51 to 53, wherein buprenorphine base is contained in an amount of from 8 to 12% by weight of the biphasic matrix layer.
55. Transdermal therapeutic system in accordance with any one of items 51 to 53, wherein buprenorphine base is contained in an amount of from 5 to 7% by weight of the biphasic matrix layer.
56. Transdermal therapeutic system in accordance with any one of items 1 to 50, wherein the active agent is diclofenac sodium.
57. Transdermal therapeutic system in accordance with item 56, wherein diclofenac sodium is contained in an amount of from 1 to 15% by weight of the biphasic matrix layer.
58. Transdermal therapeutic system in accordance with any one of items 56 or 57, wherein diclofenac sodium is contained in an amount of from 2 to 8% by weight of the biphasic matrix layer.
59. Transdermal therapeutic system in accordance with any one of items 56 to 58, wherein diclofenac sodium is contained in an amount of from 3 to 5% by weight of the biphasic matrix layer.
60. Transdermal therapeutic system in accordance with any one of items 1 to 59, wherein the biphasic matrix layer has an area weight of more than 60 $g/m^2$.
61. Transdermal therapeutic system in accordance with any one of items 1 to 60, wherein the biphasic matrix layer has an area weight of from 80 to 120 $g/m^2$.
62. Transdermal therapeutic system in accordance with any one of items 1 to 61, wherein the biphasic matrix layer has an area weight of 80 to 100 $g/m^2$.
63. Transdermal therapeutic system in accordance with any one of items 1 to 62, wherein the dissolver for the active agent is selected from the group consisting of carboxylic acids, long-chain alcohols with more than four carbon atoms, fatty alcohols, polyoxyethylene ethers of fatty alcohols, long-chain esters with more than four carbon atoms, fatty acid esters or mixtures thereof.
64. Transdermal therapeutic system in accordance with item 63, wherein the active agent is in solution in a carboxylic acid to form an active agent-carboxylic acid mixture in the discontinuous, inner phase of the biphasic matrix layer.
65. Transdermal therapeutic system in accordance with any one of items 1 to 64, wherein the biphasic matrix layer further comprises a viscosity-increasing substance.
66. Transdermal therapeutic system in accordance with item 65, wherein the viscosity-increasing substance is contained in an amount of from about 0.1% to about 8% by weight of the biphasic matrix layer.
67. Transdermal therapeutic system in accordance with any one of items 65 or 66, wherein said viscosity-increasing substance is selected from the group consisting of cellulose derivatives such as methylcellulose, ethylcellulose, hydroxyethylcellulose, hydroxypropylcellulose, hydroxypropylmethylcellulose, carboxymethylcellulose, sodium carboxymethylcellulose, microcrystalline cellulose, high molecular mass polyacrylic acids and/or their salts and/or their derivatives such as esters, polyvinylpyrrolidone, colloidal silicone dioxide, sodium alginate, tragacanth, xanthan gum, bentonite, carrageenan and guar gum, and mixtures thereof.
68. Transdermal therapeutic system in accordance with any one of items 65 to 67, wherein the viscosity-increasing substance is polyvinylpyrrolidone.
69. Transdermal therapeutic system in accordance with any one of items 1 to 68, wherein the biphasic matrix layer further comprises a viscosity-increasing substance and a carboxylic acid to form a viscosity-increasing substance-, carboxylic acid-, and active agent-containing mixture in the discontinuous, inner phase of the biphasic matrix layer.
70. Transdermal therapeutic system in accordance with any one of items 1 to 68, wherein the biphasic matrix layer is free of a viscosity-increasing substance selected from the group consisting of cellulose derivatives such as methylcellulose, ethylcellulose, hydroxyethylcellulose, hydroxypropylcellulose, hydroxypropylmethylcellulose, carboxymethylcellulose, sodium carboxymethylcellulose, microcrystalline cellulose, high molecular mass polyacrylic acids and/or their salts and/or their derivatives such as esters, polyvinylpyrrolidone, colloidal silicone dioxide, sodium alginate, tragacanth, xanthan gum, bentonite, carrageenan and guar gum, and mixtures thereof.
71. Transdermal therapeutic system in accordance with any one of items 1 to 70, wherein the dissolver for the active agent is a carboxylic acid and the carboxylic acid is contained in an amount of from 2 to 20% by weight based on the biphasic matrix layer.
72. Transdermal therapeutic system in accordance with item 71, wherein the carboxylic acid is contained in an amount of from 5 to 15% by weight based on the biphasic matrix layer.
73. Transdermal therapeutic system in accordance with item 72, wherein the carboxylic acid is contained in an amount of from 6 to 12% by weight based on the biphasic matrix layer.
74. Transdermal therapeutic system in accordance with any one of items 70 to 73, wherein the carboxylic acid and the active agent are contained in the transdermal therapeutic system in an amount ratio of from 0.3:1 to 5:1.
75. Transdermal therapeutic system in accordance with item 74, wherein the carboxylic acid and the active agent are contained in the transdermal therapeutic system in an amount ratio of from 0.5:1 to 2:1.
76. Transdermal therapeutic system in accordance with item 74, wherein the carboxylic acid and the active agent are contained in the transdermal therapeutic system in an amount ratio of from 2:1 to 5:1.
77. Transdermal therapeutic system in accordance with any one of items 69 to 76, wherein the carboxylic acid is selected from the group consisting of oleic acid, linoleic acid, linolenic acid, levulinic acid, and mixtures thereof.
78. Transdermal therapeutic system in accordance with any one of items 1 to 77, wherein the active agent-containing layer structure is an active agent-containing self-adhesive layer structure.
79. Transdermal therapeutic system in accordance with any one of items 1 to 78, wherein the biphasic matrix layer is the skin contact layer.
80. Transdermal therapeutic system in accordance with any one of items 1 to 78, wherein the active agent-containing layer structure further comprises an additional skin contact layer.
81. Transdermal therapeutic system in accordance with any one of items 1 to 6, wherein the active agent is buprenorphine, the at least one polymer is a pressure-sensitive adhesive based on polysiloxane or polyisobutylene, the emulsifier is based on polysiloxane, and the biphasic matrix layer further contains levulinic acid.
82. Transdermal therapeutic system in accordance with any one of items 1 to 6, wherein the active agent is buprenorphine, the at least one polymer is a pressure-sensitive adhesive based on polysiloxane or polyisobutylene, the emulsifier is based on polysiloxane, the biphasic matrix layer further contains levulinic acid, and wherein the levulinic acid and the buprenorphine are contained in the transdermal therapeutic system in an amount ratio of from 0.5:1 to 2:1.
83. Transdermal therapeutic system in accordance with any one of items 1 to 6, wherein the active agent is diclofenac, the at least one polymer is a pressure-sensitive adhesive based on polysiloxane or polyisobutylene, the emulsifier is based on polysiloxane, and the biphasic matrix layer further contains oleic acid.
84. Transdermal therapeutic system in accordance with any one of items 1 to 6, wherein the active agent is diclofenac, the at least one polymer is a pressure-sensitive adhesive based on polysiloxane or polyisobutylene, the emulsifier is based on polysiloxane, the biphasic matrix layer further contains oleic acid, and wherein the oleic acid and the diclofenac are contained in the transdermal therapeutic system in an amount ratio of from 2:1 to 5:1.
85. Transdermal therapeutic system in accordance with any one of items 1 to 55, and 60 to 82, providing a skin permeation rate of buprenorphine when measured in a comparable test with a commercial buprenorphine reference transdermal therapeutic system in a 96-hour time interval from hour 72 to hour 168 that is therapeutically effective.
86. Transdermal therapeutic system in accordance with any one of items 1 to 55, and 60 to 82, providing a skin permeation rate of buprenorphine when measured in a comparable test with a commercial buprenorphine reference transdermal therapeutic system in a 72-hour time interval from hour 96 to hour 168 that is therapeutically effective.
87. Transdermal therapeutic system in accordance with any one of items 1 to 55, and 60 to 82, providing a skin permeation rate of buprenorphine when measured in a comparable test with a commercial buprenorphine reference transdermal therapeutic system in a 160-hour time interval from hour 8 to hour 168 that is therapeutically effective.
88. Transdermal therapeutic system in accordance with any one of items 1 to 50, 56 to 80, 83, and 84, providing a skin permeation rate of diclofenac when measured in a comparable test with a commercial diclofenac reference transdermal therapeutic system in a 16-hour time interval from hour 8 to hour 24 that is therapeutically effective.
89. Transdermal therapeutic system in accordance with any one of items 1 to 50, 56 to 80, 83, and 84, providing a skin permeation rate of diclofenac when measured in a comparable test with a commercial diclofenac reference transdermal therapeutic system in a 40-hour time interval from hour 8 to hour 48 that is therapeutically effective.
90. Transdermal therapeutic system in accordance with any one of items 1 to 50, 56 to 80, 83, and 84, providing a skin permeation rate of diclofenac when measured in a comparable test with a commercial diclofenac reference transdermal therapeutic system in a 64-hour time interval from hour 8 to hour 72 that is therapeutically effective.
91. Transdermal therapeutic system in accordance with any one of items 1 to 55, 60 to 82, and 85 to 87, wherein the active agent is buprenorphine, for use in a method of treating pain.
92. Transdermal therapeutic system in accordance with any one of items 1 to 55, 60 to 82, and 85 to 87, wherein the active agent is buprenorphine, for use in a method of treating pain wherein the transdermal therapeutic system is applied for 7 days on the skin of a patient.
93. Transdermal therapeutic system in accordance with any one of items 1 to 50, 56 to 80, 83, 84, and 88 to 90, wherein the active agent is diclofenac, for use in a method of treating patients suffering from pain/inflammation such as osteoarthritis, shoulder periarthritis, muscle pain, low back pain, rheumatism, bruises, pulled muscles, lumbago, arthrosis, sweat gland abscess, or Multiple system atrophy.
94. Transdermal therapeutic system in accordance with item 1 to 50, 56 to 80, 83, 84, and 88 to 90, wherein the active agent is diclofenac and a therapeutically effective amount of diclofenac is provided for about 24 hours by said transdermal therapeutic system during an administration period on the skin of a human patient of about 24 hours.
95. Transdermal therapeutic system in accordance with item 1 to 50, 56 to 80, 83, 84, and 88 to 90, wherein the active agent is diclofenac and a therapeutically effective amount of diclofenac is provided for about 72 hours by said transdermal therapeutic system during an administration period on the skin of a human patient of about 72 hours.
96. Use of an emulsifier to reduce the maximum size of the dispersed deposits in a biphasic coating mixture during the process of preparing a transdermal therapeutic system in accordance with any one of items 1 to 95.
97. Use of an emulsifier to reduce the maximum size of the dispersed deposits in the biphasic matrix layer of a transdermal therapeutic system in accordance with any one of items 1 to 95.
98. Use of an emulsifier based on polysiloxane in a transdeiinal therapeutic system with an active agent-containing biphasic matrix layer having a discontinuous, inner phase and a continuous, outer phase for controlling the maximum sphere size of the discontinuous, inner phase of the biphasic matrix layer.
99. Use of an emulsifier selected from the group consisting of an emulsifier based on polyisobutylene, an emulsifier based on ethoxylated castor oil, and an emulsifier based on poloxamer in a transdermal therapeutic system with an active agent-containing biphasic matrix layer having a discontinuous, inner phase and a continuous, outer phase for controlling the maximum sphere size of the discontinuous, inner phase of the biphasic matrix layer.
100. Method of stabilizing a biphasic coating mixture that comprises a discontinuous, inner phase having a composition comprising an active agent and a dissolver for the active agent in amount sufficient so that the active agent forms a solution with the dissolver in the inner phase, the inner phase forming dispersed deposits in a continuous, outer phase comprising a polymer, by mixing the biphasic coating mixture with an emulsifier that is selected from a group consisting of emulsifiers which, when blended at about 500 to 1500 rpm with an equal weight amount of the composition of the continuous, outer phase for about 1 hour in a test tube, provide a mixture with the composition of the continuous, outer phase showing less than 20% of phase separation after storage for about 24 hours at about 20° C., determined by comparing the height of the separated phase in the test tube and the height of the total content in the test tube.
101. Stabilized biphasic coating mixture obtainable by a process in accordance with item 100, wherein the dispersed deposits in the biphasic coating mixture have a maximum droplet size of less than 55 μm.
102. Method of manufacture of a biphasic matrix layer comprising the steps of:
    (1) preparing a stabilized biphasic coating mixture in accordance with any one of items 100 or 101,
    (2) coating the stabilized biphasic coating mixture on a film in an amount to provide a desired area weight,
    (3) evaporating the solvents to provide a biphasic matrix layer with the desired area weight.
103. Biphasic matrix layer obtainable by a process in accordance with item 102.
104. Method of manufacture of a transdermal therapeutic system in accordance with any one of items 1 to 90, comprising the steps of:
    (1) providing a stabilized biphasic coating mixture comprising
        a. a polymer,
        b. an active agent,
        c. a dissolver for the active agent
        d. an emulsifier,
        e. a solvent,
        f. optionally a viscosity-increasing substance,
    (2) coating the stabilized biphasic coating mixture on a film in an amount to provide the desired area weight,
    (3) evaporating the solvents to provide a biphasic matrix layer with the desired area weight, (4) laminating the biphasic matrix layer to a backing layer to provide an active agent-containing layer structure,
(5) optionally laminating the active agent-containing layer structure to an additional skin contact layer,
(6) optionally punching the individual systems from the buprenorphine-containing self-adhesive layer structure with the desired area of release, and
(7) optionally adhering to the individual systems an active-free self-adhesive layer structure comprising also a backing layer and an active agent-free pressure-sensitive adhesive layer and which is larger than the individual systems of buprenorphine-containing self-adhesive layer structure.

105. Transdermal therapeutic system for the transdermal administration of an active agent comprising an active agent-containing layer structure, the active agent-containing layer structure comprising
A) a backing layer, and
B) a biphasic matrix layer, the biphasic matrix layer having
  a) a continuous, outer phase having a composition comprising 70 to 100% by weight of at least one polymer,
  b) a discontinuous, inner phase having a composition comprising the active agent and a dissolver for the active agent in amount sufficient so that the active agent forms a solution with the dissolver in the inner phase,
  wherein the discontinuous, inner phase forms dispersed deposits in the continuous, outer phase, and
  c) an emulsifier in an amount of 0.1 to 20% by weight based on the biphasic matrix layer,
  wherein the emulsifier is selected from the group consisting of an emulsifier based on polysiloxane, an emulsifier based on polyisobutylene, an emulsifier based on ethoxylated castor oil, an emulsifier based on poloxamer, and mixtures thereof.

The invention claimed is:

1. A transdermal therapeutic system for the transdermal administration of an active agent comprising an active agent-containing layer structure, the active agent-containing layer structure comprising:
A) a backing layer, and
B) a dried biphasic matrix layer, the dried biphasic matrix layer having
  a) a continuous, outer phase having a composition comprising 70 to 100% by weight of at least one polymer,
  b) a discontinuous, inner phase having a composition comprising the active agent and a dissolver for the active agent in amount sufficient so that the active agent forms a solution with the dissolver in the inner phase, wherein the dissolver is one or more $C_3$ to $C_{24}$ carboxylic acids;
  wherein the discontinuous, inner phase comprises spheres having a maximum sphere size of 20 µm or less dispersed in the continuous, outer phase, and
  c) an emulsifier in an amount of 0.1 to 20% by weight based on the dried biphasic matrix layer, wherein the emulsifier is a mixture of PEG/PPG-19/19 dimethicone and PEG-12 dimethicone, wherein the PEG/PPG-19/19 dimethicone is present as a dispersion containing 40 to 60% by weight of cyclopentasiloxane, and wherein the PEG-12 dimethicone and the PEG/PPG-19/19 dimethicone dispersion are present in a weight ratio of 1:1.1 to 1:2.3;
wherein the dried biphasic matrix layer does not contain a viscosity-increasing substance; and
wherein the dried biphasic matrix layer is obtained from a solvent-containing biphasic coating mixture after coating on a film and evaporating the solvent.

2. The transdermal therapeutic system in accordance with claim 1, wherein the dried biphasic matrix layer contains 0.1 to less than 20% by weight of the emulsifier.

3. The transdermal therapeutic system in accordance with claim 1, wherein the at least one polymer in the continuous, outer phase is polysiloxane or polyisobutylene.

4. The transdermal therapeutic system in accordance with claim 1 wherein the at least one polymer in the continuous, outer phase is a pressure-sensitive adhesive polymer.

5. The transdermal therapeutic system in accordance with claim 1, wherein the dried biphasic matrix layer contains from 1 to 30% the active agent by weight of the dried biphasic matrix layer.

6. The transdermal therapeutic system in accordance with claim 1, wherein the active agent is selected from the group consisting of buprenorphine and diclofenac.

7. The transdermal therapeutic system in accordance with claim 1, wherein the dried biphasic matrix layer has an area weight of more than 60 g/m².

8. The transdermal therapeutic system in accordance with claim 1, wherein the dissolver for the active agent is selected from the group consisting of oleic acid, linoleic acid, linolenic acid, levulinic acid, and mixtures thereof.

9. The transdermal therapeutic system in accordance with claim 1, wherein the dried biphasic matrix layer contains from 2 to 20% the one or more $C_3$ to $C_{24}$ carboxylic acids by weight of the dried biphasic matrix layer.

10. The transdermal therapeutic system in accordance with claim 1, wherein the active agent-containing layer structure is an active agent-containing self-adhesive layer structure, and wherein the dried biphasic matrix layer is the skin contact layer.

11. A method of treating pain in a patient in need thereof, the method comprising applying the transdermal therapeutic system in accordance with claim 1 for 7 days on the skin of the patient, and wherein the active agent is buprenorphine.

* * * * *